US006204436B1

(12) United States Patent
Mannerloef et al.

(10) Patent No.: US 6,204,436 B1
(45) Date of Patent: Mar. 20, 2001

(54) TRANSGENIC PLANTS

(75) Inventors: Marie Mannerloef; Paul Peter Tenning, both of Helsingborg (SE); Per Steen, Stubbekoebing (DK)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/182,117

(22) Filed: Oct. 29, 1998

Related U.S. Application Data

(60) Provisional application No. 60/112,003, filed on Oct. 31, 1997.

(51) Int. Cl.$^7$ ............................. C12N 5/04; C12N 15/82; C12N 15/90; A01H 5/00; A01H 5/10
(52) U.S. Cl. ..................... 800/300; 435/418; 435/419; 435/468; 800/278; 800/294
(58) Field of Search ................ 435/69.1, 320.1, 435/410, 418, 419, 468, 469; 536/23.7; 800/278, 288, 294, 295, 298, 300

(56) References Cited

U.S. PATENT DOCUMENTS

| | | | |
|---|---|---|---|
| 4,535,060 | 8/1985 | Comai | 435/320.1 |
| 4,769,061 | 9/1988 | Comai | 800/300 |
| 4,940,835 | 7/1990 | Shah et al. | 800/300 |
| 4,971,908 | 11/1990 | Kishore et al. | 435/468 |
| 5,094,945 | 3/1992 | Comai | 435/468 |
| 5,145,783 | 9/1992 | Kishore et al. | 435/320.1 |
| 5,188,642 | 2/1993 | Shah et al. | 47/58.1 |
| 5,312,910 | 5/1994 | Kishore et al. | 536/23.2 |
| 5,463,175 | 10/1995 | Barry et al. | 800/300 |
| 5,508,468 | 4/1996 | Lundquist et al. | 800/320.1 |
| 5,510,471 | 4/1996 | Lebrun et al. | 536/23.4 |
| 5,538,877 | 7/1996 | Lundquist et al. | 435/468 |
| 5,538,880 | 7/1996 | Lundquist et al. | 435/468 |
| 5,550,318 | 8/1996 | Adams et al. | 800/278 |
| 5,554,798 | 9/1996 | Lundquist et al. | 800/300.1 |
| 5,627,061 | 5/1997 | Barry et al. | 435/468 |
| 5,631,152 | 5/1997 | Fry et al. | 435/468 |
| 5,633,435 | 5/1997 | Barry et al. | 800/300 |
| 5,776,760 | 7/1998 | Barry et al. | 435/252.3 |
| 5,804,425 | 9/1998 | Barry et al. | 435/193 |
| 5,859,348 | 1/1999 | Penner et al. | 800/300 |

FOREIGN PATENT DOCUMENTS

| | | | |
|---|---|---|---|
| WO 95/06128 | 3/1995 | (WO) | C12N/15/82 |
| WO 98/39419 | 3/1997 | (WO) | C12N/5/14 |
| WO 97/36488 | 10/1997 | (WO) | A01N/57/20 |
| WO 98/44140 | 10/1998 | (WO) | C12N/15/82 |

OTHER PUBLICATIONS

Jacq et al, Plant Cell Rep., vol. 12, pp. 621–624, 1993.*
Catlin, D.W., Plant Cell Rep., vol. 9, pp. 285–288, 1990.*
McGarvey et al, Biotechniques, vol. 11, pp. 428–432.*

Boudry et al., "The origin and evolution of weed beets: consequences for the breeding and release of herbicide–resistant transgenic sugar beets," Theor. Appl. Genet. 87: pp. 471–478 (1993).

D'Halluin et al., "Transformation of Sugarbeet (*Beta Vulgaris* L.) and Evaluation of Herbicide Resistance in Transgenic Plants," Bio/Technology, 10: pp309–314 (1992).

Mannerloef et al., "Transgenic sugar beet tolerant to glyphosate," Euphytica, 94: pp83–91 (1997).

Pedersen and Steen, "The Stability of Transgenes Inserted into Sugarbeet (*Beta Vulgaris* L.), " 58$^{th}$ Congress of the International Institute for Beet Research at the French Technical Institute for Sugar Beet: pp. 197–200 (Jun. 1995).

Steen and Pedersen, "Gene Transfer for Herbicide Resistance," Journal of Sugar Beet Research, 30(4): pp. 267–273 (1993).

Steen and Pedersen, "Strategies in Creating Transgenic Herbicide Tolerant Sugarbeet (*Beta Vulgaris* L.) Varieties." 58$^{th}$ Congress of the International Institute for Beet Research at the French Technical Institute for Sugar Beet: pp. 189–192 (Jun. 1995).

Steen and Pedersen, "Yield and Quality Characters in Transgenic Herbicide Tolerant Sugarbeet (*Beta Vulgaris* L.)," 58th Congress of the International Institute for Beet Research at the French Technical Institute for Sugar Beet: pp. 185–188 (Jun. 1995).

Steen et al., "Roundup Ready™ Sugar Beet," 58th Congress of the International Institute for Beet Research at the French Technical Institute for Sugar Beet: pp. 557–559 (Jun. 1995).

Tenning et al., "Glyphosate Tolerance in Transgenic Sugar Beet," 58th Congress of the International Institute for Beet Research at the French Technical Institute for Sugar Beet: p. 183 (Jun. 1995) absrtact.

Wells, B. H., "Development of Glyphosate Tolerant Crops Into the Market," Chemical Abstracts, 124(8): abstract No. 79375 (1996).

* cited by examiner

*Primary Examiner*—Gary Benzion
*Assistant Examiner*—Ashwin D. Mehta
(74) *Attorney, Agent, or Firm*—Larry W. Stults; Bruce Vrana

(57) ABSTRACT

The present invention relates to transgenic sugar beet plants which due to the expression of cp4/epsps enzyme activity tolerate treatment with about 4 to about 18 liters Roundup® per hectar. The plants can be characterized by theis specific integration site. The invention further relates to seeds obtained from said plants and a method for producing said plants.

8 Claims, No Drawings

TRANSGENIC PLANTS

This U.S. application Ser. No. 09/182,117 claims the benefit of U.S. application Ser. No. 60/112,003, filed Oct. 31, 1997.

The present invention relates to transgenic sugar beet plants capable of tolerating herbicide treatment with glyphosate as active ingredient.

Weeds in sugar beet fields are a major problem for the farmer. They compete with the crop thus reducing yield. Today, no single herbicide is able to effectively control all weeds without harming the sugar beet crop itself (Miller et al, J. Sugar Beets Res. 26: 3–4, 1989). In practice, farmers use mixtures of herbicides, which also reduce growth of the crop. Meanwhile the number of weed species having developed resistance to said herbicides continues to increase (Schweizer et al, J. of Sugar Beet Research 28: 1–23, 1991) thereby aggravating the problem of weed control in sugar beet fields.

Roundup® is a broadspectrum, environmentally preferable herbicide inhibiting the growth of both weed and crop species. In the context of the present invention one liter of a herbicidal Roundup® solution comprises 360 g of its active ingredient (a.i.) glyphosate (the common name of N-phosponomethyl-glycine) which is taken up by foliage. So far no glyphosate resistant weed has developed in over 20 years of use (Holt et al., Annu. Rev. Plant Physiol., 1993); additionally no natural tolerance to glyphosate has been found in sugar beet. However, pre-emergence use of Roundup® seems to be more efficient for weed control in sugar beet fields than a combination of herbicides often used in sugar beet agriculture, consisting of phenmediphan, metamitron and ethofumesate (Madsen et al, Weed Res. 35: 105–111, 1995).

Glyphosate inhibits the biosynthesis of aromatic amino acids, through irreversible binding to 5-enolpyruvylshikimate-3-phosphate synthase (epsps). Within the chloroplast this enzyme catalyzes the reaction of shikimate-3-phosphate and phosphoenolpyruvate to form 5-enolpyruvylshikimate-3-phosphate and phosphate. Approximately one week after application of the herbicide, visible effects can be seen including wilting, yellowing followed by complete browning, deterioration of plant tissue, and decomposition of the roots.

To impart glyphosate tolerance to crop species, focus has been on the introduction into plants of epsps genes capable of increasing glyphosate tolerance. Besides plants bacteria and fungi naturally express epsps enzyme activity. The cp4/epsps from Agrobacterium sp.

CP4 was found to confer tolerance to glyphosate (Barry et al., "Inhibitors of Amino Acid Biosynthesis: Strategies for Imparting Glyphosate Tolerance to Crop Plants", in: Biosynthesis and Molecular Regulation of Amino Acids in Plants, Singh et al (eds), American Society of Plant Physiologists, pages 139–145, 1992). Introduction of the cp4/epsps gene into soybean and oilseed rape yielded tolerance to foliar application of the herbicide under field conditions (Delannay et al., Crop Sci. 35: 1461–1467, 1995; Padgette et al., Crop Sci. 35: 1451–1461, 1995).

Glyphosate oxidase reductase (gox) isolated from Achromobacter sp. strain LBAA (Barry etal., supra) degrades glyphosate into aminomethyl phosphonic acid, a compound non-toxic for the plant. A combination of the cp4/epsps and glyphosate oxidase (gox) genes has been successfully used to obtain transgenic wheat (Zhou et al., Plant Cell Rep. 15: 159–163, 1995) tolerant to glyphosate.

SUMMARY OF THE INVENTION

The object of the present invention is to provide sugar beet plants which tolerate glyphosate in doses sufficiently high to effect optimal herbicidal activity. Such plants can be further improved by backcrossing with elite sugar beet lines to optimize agronomic properties such as yield, pathogen resistance, etc.

Sugar beets may be transformed using *Agrobacterium tumefaciens* mediated transformation (Fry et al, Third international congress of plant mol. biol., Tuscon, Arizona, USA; D'Halluin et al, Bio/Technology 10: 309–314, 1992; Konwar, J. Plant Biochem & Biotech 3: 37–41, 1994). Agrobacterium-mediated transformation often results in more than one copy of the T-DNA being integrated into the plant's genome. The gene to be integrated is preferably introduced into the T-DNA such that it becomes located close to the T-DNA right border which, contrary to the left border, will almost always be transferred to the plant.

Plants according to the present invention tolerate treatment with more than about 3×6 liters of the herbicide Roundup® per hectar (about 18 liters per hectar). The total standard dose to obtain good weed control varies between 4 and 6 liters per hectare, depending on weed pressure. At these concentrations herbicide treatment exerts no detectable effect on plant vigour and leaf chlorosis. The tolerance exhibited by the plants according to the invention is conferred by a transgenically expressed cp4/epsps enzyme activity. A preferred embodiment of the present invention has been deposited with the National Collections of Industrial and Marine Bacteria Limited (23 St Machar Drive, Aberdeen AB2 1 RY, Scotland UK) on Oct. 24, 1997, under the Accession No. 40905. The deposit has been deposited under the Budapest Treaty and will be irrevocably and without restriction or condition be released to the public upon the issuance of the patent.

The present invention thus relates to a sugar beet plant including the descendants thereof expressing cp4epsps enzyme activity. In particular the invention relates to a sugar beet plant including the descendants thereof tolerating the treatment with about 4 to about 18 liters Roundup® per hectar.

Plants according to the present invention can be obtained by routine Agrobacterium mediated transformation using a transformation vector comprising between right and left T-DNA border sequences a piece of DNA as described in SEQ ID NO: 5 encoding i.a. cp4/epsps.

It was surprisingly found within the scope of the present invention, that a transformation event (RRMax) lacking left and right T-DNA border sequences within the transgenic genome and resulting in deletion of a considerable part of the transformation vector DNA while retaining the cp4/epsps encoding DNA provides superior glyphosate tolerance. In particular a piece of DNA as characterized by SEQ ID NO: 1 is found integrated into a highly repetitive region of the genome simlutaneously replacing part of said repetitive genomic sequence. The genomic DNA directly adjacent to that part of the transgene sequence which in the transformation vector used is linked to the T-DNA right border sequence, has the sequence given in SEQ ID NO: 2. The genomic DNA directly adjacent to the other end of the integrated transgenic DNA has the sequence given in SEQ ID NO: 3. The complete DNA sequence of the newly formed genomic DNA arrangement is given in SEQ ID NO: 4.

Accordingly, the present invention relates to a sugar beet plant including the descendents thereof wherein DNA characterized by the nucleotide sequence of SEQ ID NO: 1 forms part of the plant's genome and said nucleotide sequence preferably replaces highly repetitive DNA sequences within the plant's genome.

Preferred herein is a sugar beet plant including the descendents thereof wherein those parts of the genome directly linked to said nulceotide sequence are characterized by the nucleotide sequences of SEQ ID NO: 2 and SEQ ID NO: 3, resepctively.

Further preferred is a sugar beet plant including the descendents thereof wherein DNA characterized by the nucleotide sequence of SEQ ID NO: 4 forms part of the plant's genome.

The herbicide tolerance engineered into the transgenic seeds and plants mentioned above are passed on by sexual reproduction or vegetative growth and can thus be maintained and propagated in descendant plants. Generally said maintenance and propagation make use of known agricultural methods developed to fit specific purposes such as tilling, sowing or harvesting. As the growing crop is vulnerable to attack and damages caused by insects or infections, measures are undertaken to control plant diseases, insects, nematodes, and other adverse conditions to improve yield. These include mechanical measures such a tillage of the soil or removal of infected plants, as well as the application of agrochemicals such as fungicides, gametocides, nematicides, growth regulants, ripening agents and insecticides.

Use of the herbicide tolerance of the transgenic plants and seeds according to the invention can further be made in plant breeding which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD®), methalaxyl (Apron®), and pirimiphos-methyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods such as the methods exemplified above which are characterized by the use of transgenic plants, transgenic plant material, or transgenic seed according to the present invention.

In another embodiment, the present invention relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

The invention further relates to a commercial bag containing Roundup® tolerant sugar beet seed capable of expressing cp4/epsps, together with lable instructions for the use thereof. Preferred within this invention is a commercial bag comprising seed of a transgenic plant comprising stably integrated into its genome a piece of DNA having the nucleotide sequence depicted in SEQ ID NO: 1. The transformation methodology employed can be summarized as follows:

(a) transforming in vitro grown sugar beet cotyledons using *Agrobacterium tumefaciens* with a vector comprising a piece of DNA encoding cp4/epsps such as described in SEQ ID NO: 5;

(b) regenerating shoots in the presence of glyphosate;

(c) transferring the shoots to soil in the greenhouse;

(d) treating plantlets with glyphosate;

(e) visually grading plant vigour and leaf chlorosis;

(g) selecting completely normal plants with normal vigour and leafes uneffected by glyphosate treatment; and (h) propagating the selected plants using conventional breeding techniques.

In particular shoots are regenerated in the presence of about 0.1 to about 10 mM, preferably about 1 mM glyphosate after 8–12 weeks of selection. Each transgenic shoot is further propagated into ten copies which can optionally be analyzed for the presence of the cp4/epsps transgene using polymerase chain reaction (PCR) before it is transferred to the greenhous for rooting. Light conditions in the greenhouse are 16 hours of light and 8 hours of darkness with a temperature of 22±2° C. At the three to four leaf stage, the plantlets are sprayed with an aqueous solution of Roundup® at a dose of 0.1 to 20 liters, preferably 1 liter per hectar. Visual injury ratings for plant vigour and plant chlorosis based on a scale from 0 (dead plant) to 9 (completely uneffected plant) are taken on individual plants 2 weeks after glyphosate application. Ratings of 0 to 3 are characteristic of susceptible plants. Ratings of 3 to 7 indicate a low to intermediate level of tolerance, and ratings of 8 or 9 indicate good levels of tolerance. In particular the the ratings have the following meaning:

9 . . . Unaffected plant identical to untreated control

8 . . . Only very small necrosis on the tips of the leaves with less than 5% of the leaf area affected and yellow 7 . . . Very small necrosis on the tips of the leaves which start to curl; less than 5% of the leaf area are affected and yellow 6,5,4 . . . Increasing necrosis and leaf curl; leaves are becoming smaller than normal 3,2 . . . No or very limited leaf growth; all leaves are curled and affected by necrosis 1 . . . No growth of the plant; up to 5% of the plant stay green 0 . . . Dead plant To collect data from field trials plants with normal vigour and uneffected by glyphosate treatment (rating 9) are further propagated or bred by convential techniques.

Transformation is preferably performed using a Ti vector comprising a piece of DNA with the sequence given in SEQ ID NO: 5 containing the cp4/epsps and gox genes both of which have been reported to confer tolerance to glyphosate in certain plant species, and the reporter gene uidA encoding the β-glucuronidase enzyme. The enhanced 35S promoter (Odell et al., Nature 313: 810–812, 1985) is linked to the uidA gene, the figworth mosaic virus (FMV) promoter (Gouwda et al., J. Cell. Biochem. Suppl. 13D: 301, 1989) to the cp4/epsps and gox genes. Upstream of the cp4/epsps and the gox genes a transit peptide (Gasser et al., J. Biol. Chem. 263:4280–4289, 1988) is inserted to achieve targeting of both of the proteins to the chloroplast.

One transformation event which was generated in accordance with the present invention is surprisingly found to be uneffected by doses of up to about 3×6 liters (about 18 liters) of the herbicide Roundup® per hectar. Molecular analysis reveals that there is a single copy of transgenic DNA integrated at a single locus;

the integrated DNA encodes cp4/epsps and corresponds to truncated vector DNA;

the integrated DNA replaces a piece of genomic DNA and has the sequence shown in SEQ ID NO: 1;

the genomic DNA directly adjacent to the integrated DNA is characterized by the sequences of SEQ ID NO: 2 and SEQ ID NO: 3 resulting in the new genomic sequence arrangment of SEQ ID NO: 4;

the cp4/epsps and the uidA genes are intact whereas the gox gene is truncated;

other vector sequences are not present in the transgenic plants.

Now that this information is available plants derived from one of the specific transformation events according to the invention can be easily distnguished from other sugar beet plants by means of PCR. Suitable primer pair combinations allow to specifically identify genomic DNA sequences which are only present in plants directly or indirectly resulting from identical transformation events. Such events are not in any way limited to those obtained by Agrobacterium-mediated transformation but may also result from biolistic transformation experiments.

The present invention thus further relates to a sugar beet plant including the descendents thereof characterized in that PCR amplification with its genomic DNA as template results in amplification of a 739 bp DNA fragment when using a pair of oligonucleotide primers characterized by the sequences of SEQ ID NO: B and SEQ ID NO: a; or a 834 bp DNA fragment when using a pair of oligonucleotide primers characterized by the sequences of SEQ ID NO: D and SEQ ID NO: e; or a 1057 bp DNA fragment when using a pair of oligonucleotide primers characterized by the sequences of SEQ ID NO: A and SEQ ID NO: b; or a 1224 bp DNA fragment when using a pair of oligonucleotide primers characterized by the sequences of SEQ ID NO: C and SEQ ID NO: f.

DETAILED DESCRIPTION OF THE INVENTION

EXAMPLES

The following examples further describe the materials and methods used in carrying out the invention and the subsequent results. They are offered by way of illustration, and their recitation should not be considered as a limitation of the claimed invention.

Example 1

Sugar Beet Transformation

Sugar beet of genotype A1012 is transformed with a vector containing a cp4/epsps and a gox gene capable of confering glyphosate tolerance, the nptll gene, which confers resistance to the antibiotic kanamycin and the reporter gene uidA encoding β-glucuronidase (GUS). The nptil and the uidA gene are functionally linked to the enhanced 35S promoter (Odell et al., Nature 313: 810–812,1985) whereas the cp4/epsps and gox genes are under control of the the figworth mosaic virus (FMV) promoter (Gouwda et al., J. Cell. Biochem. Suppl. 13D: 301, 1989). Additionally the cp4/epsps and gox gene are linked to a transit peptide (Gasser et al., J. Biol. Chem. 263: 4280–4289,1988) positioned 5' to target both proteins to the chloroplast. cp4/epsps and uidA make use of the E9 3' terminator sequences whereas gox and nptll use the corresponding NOS 3' sequence. In vitro grown sugar beet (*Beta vulgaris*. L) are transformed using *A. tumefaciens*. Plants are regenerated as described by Fry et al. ("Genotype-independent transformation of sugarbeet using *Agrobacterium tumefaciene*", Third international congress of plant mol. biol., Tuscon, Ariz., USA.,1991) and Konwar (J. Plant Biochem & Biotech 3: 37–41, 1994) using glyphosate at a concentration of 1 mM as selection agent. In order to eliminate *A. tumefaciens* the cotyledons are three times incubated in MS medium containing 500 mg/lit cefotaxime (60 min at 45–50 rpm). Regenerated shoots are analyzed after 8–12 weeks of selection on 1 mM glyphosate, 500 mg/lit cefotaxime including passage to fresh media every third week. Each transgenic shoot is further micropropagated into ten copies, analyzed for the presence of the transgene, and transferred to the greenhouse for rooting.

Polymerase Chain Reaction (PCR) is used to verify the presence of the cp4/epsps gene. Twenty mg of plant material is collected in an eppendorf tube from regenerated in vitro shoots. Total DNA is extracted essentially according to Tai et al, Plant Mol. Biol. Rep 8: 297–303, 1990. Minor modifications are adding 500 µl of 100 mM Tris-HCl pH 8.0 containing 50 mM Na-EDTA, 1,25% SDS (W/V), 0,38% Na-Bisulfite (W/V), and 200 jg/ml proteinase K and incubating at 65° C. for two hours. Undissolved leaf material is hooked out and total DNA precipitated and frozen for 2 hours at –20° C. PCR is performed according to the instructions included with the Perkin-Elmer Gene-Amp PCR kit (Perkin-Elmer Corp.) using a modified 10× reaction buffer consisiting of 100 mM Tris-HCl pH 8.3, 500 mM KCl, 30 mM $MgCl_2$, 1.0% Nonidet P-40 (W/V), 0.4 µM cresol red in 24% sucrose (W/V) and the Taq Start Antibody (Clontech). For amplifying cp4/epsps sequences the following primers are used (Shah et al., Science 233: 478–481, 1986):

5'-CAC CGG TCT TTT GGA AGG TGA AG-3' (SEQ ID NO: 6) and

5'-AAC GAG ACC CAT AAC GAG GAA GC-3' (SEQ ID NO: 7). For amplifying a genomic internal control sequence (surA, surB) the following primers are used:

5'-AAA CAG TCC CGT GCA TCC CCA AC-3' (SEQ ID NO: 8) and

5'-GAC GCT CTC CTT GAT TCT GTC CC-3' (SEQ ID NO: 9).

No variation in transformation efficiency is seen between different binary plasmids.

Micropropagated shoots are transferred to soil in the greenhouse. Light conditions in the greenhouse are 200 $\mu$mol m$^{-2}$ sec$^{-1}$, (Osram Power Star HQI-Z, 400W), 16 hours of light, 8 hours of darkness, and a temperature of 22±2° C. At the three to four leaf stage plantlets derived from 260 independent transformants are treated with Roundup®. A calibrated sprayer is used to apply an aqueous solution of the herbicide at a dose of 1 lit per ha. (360 g.a.i.l$^{-1}$)). Visual injury ratings for phytotoxic effects, based on a scale from 0 (complete leaf necrosis) to 9 (no visible effects) are taken on individual plants 2 weeks after glyphosate application. For 75 different transformants phytotoxic effects ranging from score 0–6 are detected. The other 185 (71%) transformants score 7 or more which means they show minor or no visible effects after treatment with the herbicide. Those are further crossed with non-transgenic sugar beets to produce F1 progeny for subsequent evaluation in field trials.

Field trials are performed to evaluate the different transformation events under field conditions. The plots consist of three rows, each row 9 meter long, with a distance between the rows of 0.5 meter. One individual transformant is drilled in each plot. After an initial is Roundup® application of 1 lit per ha (360 g a.i.l$^{-1}$), at the cotyledon stage, to eliminate non-transgenic segregating plants, the rows are singled by hand, to a final stand of 1 plant per 20 centimeter. Each plot is divided in three parts that are treated independently. One plot is treated with the conventional herbicides metamitron 0.1 kg a.i.ha$^{-1}$, phenmediphan 0.2 kg a.i.ha$^{-1}$ and ethofumesate 0.1 kg a.i.ha$^{-1}$. The other plot is treated with 2 times 2 lit per ha (1440 g a.i.l$^{-1}$) of Roundup® and the third plot is treated with 2 times 4 liter (2880 g a.i.l$^{-1}$) of Roundup®. The plants are treated at the two leaf stage and at the four leaf stage. Two weeks after the last application, the plants are scored for phytotoxic effects due to herbicide application. Symptoms ranging from complete susceptibility to complete tolerance are found. Differences between scoring in the greenhouse and scoring in the field trial are observed. This is probably due to environmental differences between the greenhouse and the field trial including absence of UVB light under glass. There were no morphological or physiological changes between plants from plots treated with different doses of Roundup®, compared to treatments with a conventional herbicide mixture. Two transformants show high tolerance to Roundup® after treatment with 2 times 2 lit and 2 times 4 lit per ha.

After spraying with Roundup®, tolerance was measured by grading for plant vigour (Tr.vig) and leaf chlorosis (Tr.chl). The various grades have the following meaning:

9 . . . Unaffected plant identical to untreated control

8 . . . Only very small necrosis on the tips of the leaves with less than 5% of the leaf area affected and yellow 7 . . . Very small necrosis on the tips of the leaves which start to curl; less than 5% of the leaf area are affected and yellow 6,5,4 . . . Increasing necrosis and leaf curl; leaves are becoming smaller than normal 3,2 . . . No or very limited leaf growth; all leaves are curled and affected by necrosis 1 . . . No growth of the plant; up to 5% of the plant stay green 0 . . . Dead plant 22 different transformation events (Entry 1–22) and 1 non-transgenic control (Entry 23) are sprayed with 1+4+4 liters of Roundup®/Ha (Total 9 l/Ha). The results of the visual injury rating are given in the following table.

| Entry | Vigour Rating | Chlorosis Rating | |
|---|---|---|---|
| 1 | 9 | 9 | (RRMaX) |
| 2 | 6 | 7 | |
| 3 | 2 | 3 | |
| 4 | 5 | 7 | |
| 5 | 9 | 8 | |
| 6 | 3 | 3 | |
| 7 | 7 | 7 | |
| 8 | 7 | 8 | |
| 9 | 4 | 6 | |
| 10 | 5 | 6 | |
| 11 | 5 | 5 | |
| 12 | 4 | 5 | |
| 13 | 9 | 9 | |
| 14 | 3 | 5 | |
| 15 | 4 | 4 | |
| 16 | 2 | 3 | |
| 17 | 1 | 1 | |
| 18 | 2 | 2 | |
| 19 | 6 | 8 | |
| 20 | 7 | 5 | |
| 21 | 4 | 5 | |
| 22 | 5 | 7 | |
| 23 | 0 | 0 | (non-transgenic control) |

Example 2

Copy Number of the Integrated Transgenic DNA

The copy number of the transgenic DNA integrated within the genome of the transformant with the highest glyphosate tolerance (RRMax) is determined by Southern blot analysis of restriction fragments extending beyond the right and left border sequences of the transformation vector used.

Genomic DNA from RRMax and a non-transgenic plant with the same genetic is isolated from 250 mg of freeze dried sugar beet leaf material according to Saghai-Maroof et al., Proc. Natl. Acad. Sci. USA 81:8014–8018, 1984. DNA of the transformation vector used serves as the positive control. 15 $\mu$g of DNA are digested with 120 units of restriction enzyme for 4 hours at 37° C. in a total volume of 400 $\mu$l. The digested DNA is precipitated and redissolved in a total volume of 50 $\mu$l. Digested DNA, positive plasmid control, and molecular marker size standard (Lambda digested with EcoRI and HindIII) are separated on a 0.8% agarose gel. DNA is visualized with ethidium bromide and a photograph including a ruler is taken. The DNA is then transferred onto a Hybond N+ membrane and hybridized to the probe as described by Ausubel et al. (eds.) in: "Current protocols in molecular biology", Green Publishing Associates, Inc. and John Wiley & Sons, Inc., New York, 1987.

Probes complementary to basepairs 975–1766 of the cp4/epsps gene sequence (SEQ ID NO: 5) and basepairs 7108–7535 of the gox gene sequence (SEQ ID NO: 5) are prepared by Polymerase Chain Reaction (PCR) wherein the transformation vector used serves as the template DNA for the reaction. The cp4/epsps probe is used to determine the number of inserts flanking the right border region. The gox probe is used to determine the number of inserts flanking the left border region. The PCR products are purified using the Geneclean II® Kit of BIO 101 (La Jolla, Calif.). Labelling of the probe with $^{32}$P is achieved making use of the Megaprime™ DNA labelling system of Amersham International (Little Chalfont, UK).

Determination of copy number can be performed by analysis of genomic DNA flanking the right border region. Genomic DNA is digested with the restriction enzyme Ncol which cuts the plasmid derived sequences between the 35S promoter and the uidA gene and within the sugar beet genome. The membrane is probed with the internal PCR fragment from the cp4/epsps gene. After digestion with Ncol and hybridizing with the cp4/epsps probe, a single band of 4.7 kb is detected in RRMax. This demonstrates a single copy of transferred DNA at a single locus.

Determination of copy number can also be performed by analysis of genomic DNA flanking the left border region.

screen for putative clones covering the integration event. A total of 25 phages are detected which hybridize to the cp4epsps or the gox probe. Two clones are found to hybridize to the cp4/epsps probe and the gox probe, respectively. One of them is purified (Fritsch et al.,1987) and further evaluated by Southern blot analysis and PCR. It contains a 15–16 kb insert of genomic DNA including the transgenic DNA and the flanking sugar beet sequences. Said flanking sequences are amplified by PCR using a primer matching FMV promoter or gox gene sequences in combination with a primer matching a sequence in the λFIXII cloning cassette (detailed sequences are given in Table 1 below). The integrated DNA/sugar beet junction regions are sequenced by the Sanger dideoxy-mediated chain-termination method using Applied Biosystems, Model 373A,Version 2.1.1. The primers used for sequencing are given in Table 2.

TABLE 1

Primers used for the amplification of the border regions

| Primer | Sequence | |
|---|---|---|
| #3 | 5'-CAAGAAGGTTGGTATCGCTG-3' | (SEQ ID NO: 10) |
| #7 | 5'-TCTTTTGTGGTCGTCACTGCGTT-3' | (SEQ ID NO: 11) |
| #8 | 5'-GCGAGCTCTAATACGACTCACTAT-3' | (SEQ ID NO: 12) |
| #9 | 5'-CGCGAGCTCAATTAACCCTCACT-3' | (SEQ ID NO: 13) |

TABLE 2

Sequencing primers

| Primer | Sequence | | Description |
|---|---|---|---|
| S1 | 5'-TCTGTACCCTGACCTTGTTG-3' | (SEQ ID NO: 14) | to sequence the flanking right border region |
| S3 | 5'-CGTGGATACCACATCGTGAT-3' | (SEQ ID NO: 15) | to sequence the flanking left border region |
| S4 | 5'-ACCTTGGCTTGAAGTACTC-3' | (SEQ ID NO: 16) | to sequence the flanking left border region |

Genomic DNA is digested with the restriction enzyme HindIII which cuts the plasmid derived sequences between the E9 3' terminator of the uidA gene and the FMV promoter of the gox gene and within the sugar beet genome. After digestion with HindIII and hybridizing with the gox probe, a single band of approximately 2.0 kb is detected for the transformant RRMax. Since the minimum expected fragment size is ≧4.4 kb, the result indicates a truncation of the plasmid DNA during the transfer into the genomic DNA of the plant. Nevertheless, the result confirms that only a single copy of transferred DNA is integrated at a single locus.

Example 3

Sequence Analysis of the RRMax Integration Site

Genomic RRMax DNA is isolated from 250 mg of freezed dried sugar beet leaf material according to Saghai-Maroof et al. supra. A λFIXII phage library with insert sizes of 9–23 kb in an XhoI cloning site is made (ordered with Stratagene) and probed with cp4/epsps and gox probes to Sequence analysis revealed that the transgenic DNA integrated in the genome of RRMax has the nucleotide sequence given in SEQ ID NO: 1. The integration start point lies between the right border sequence and the FMV promoter and terminates 897 basepairs downstream of the gox start-codon. Translational stop codons for the truncated gox gene can be found 130 and 235 basepairs downstream of the junction site. A HindIII site is identified 210 basepairs downstream and a transcriptional termination signal (AATAAA) 650 basepair downstream of the gox start codon. SEQ ID NO: 2 describes the DNA sequence of the genomic DNA directly linked to the right border region of the transgenic DNA and SEQ ID NO: 3 the DNA sequence of the genomic DNA directly linked to the left border region of the transgenic DNA.

Example 4

Characterization of the Transgenic DNA Integrated by RRMax

To further characterize the right border region, genomic DNA of RRMax and transformation vector DNA are digested with either restriction enzyme BamHI, HindIII, BclI or EcoRI. In southern blot analysis the cut DNA is probed with the cp4/epsps PCR fragment described in Example 2. Independent of the restriction enzyme used, digestion with the different restriction enzymes gives rise to a single fragment in Southern blot analysis. The size of the fragments detected are indicated in Table 3. The data demonstrate that a single copy of the DNA was transferred to the plant, and that the DNA transfer into the sugar beet plant resulted in complete transfer of the cp4/epsps gene. The results are in agreement with the results of the copy number determination in example 2 and the nucleotide sequence analysis of example 3.

TABLE 3

Southern blot fragment sizes

| Enzyme | RRMax | transformation vector |
|--------|-------|----------------------|
| BamHI  | >10 kb | 9.7 kb |
| HindIII | 2.4 kb | 2.4 kb |
| BclI   | 3.2 kb | 2.9 kb |
| EcoRI  | 1.8 kb | 1.8 kb |

To further characterize the piece of transgenic DNA integrated, genomic DNA from RRMax is digested with either restriction enzyme NcoI, BamHI or HindIII. As a control Transformation vector DNA is digested with the same restriction enzymes. The blot is probed with a PCR amplified DNA fragment spanning basepairs 3796–4837 of the uidA gene in SEQ ID NO: 5. The size of the fragments detected is indicated in Table 4. Independent of restriction enzyme used, digestion with the different restriction enzymes gives rise to a single signal on the autoradiographic film demonstrating that the DNA insert has the same characteristics as the internal DNA of the transformation vector used.

TABLE 4

Southern blot fragment sizes

| Enzyme | transformation vector | RRMax |
|--------|----------------------|-------|
| NcoI   | 3.4 kb | 3.4 kb |
| BamHI  | 3.2 kb | 3.2 kb |
| HindIII | 3.2 kb | 3.2 kb |

To further characterize the left border region, genomic DNA of RRMax and transformation vector DNA are digested with either restriction enzyme NcoI, BamHI, HindIII or EcoRI. In southern blot analysis the cut DNA is probed with the gox PCR fragment described in Example 2. The size of the fragments detected is indicated in Table 5. Independent of restriction enzyme used, digestion with the different restriction enzymes gives rise to a single fragment fragment on the autoradiographic film. Digestion with either restriction enzyme NcoI, BamHI or EcoRI is expected to identify an internal fragment of a known size. However, none of these restriction enzymes gives rise to such an internal fragment of the expected size. This indicates that the restriction sites for NcoI, BamHI, and EcoRI are absent in the transgenic plant. The results are in agreement with the results obtained by sequencing where it was found that the gox gene was only partly integrated in the plant. Digestion with restriction enzyme HindIII gives rise to a fragment of approximately 2 kb additionally confirming the sequencing data where a HindIII site is located downstream the gox gene in the genome. The results also show that a single copy of the transgenic DNA has been transferred to the plant. They correlate well to the primary results of the copy number determination in example 2 and the nucleotide sequence analysis in example 3. A single copy is integrated in the plant genome whereas the gox gene is partly deleted.

TABLE 5

Southern blot fragment sizes

| Enzyme | transformation vector | T9100152 |
|--------|----------------------|----------|
| NcoI   | 2.5 kb | 3.0 kb |
| BamHI  | 2.9 kb | >10 kb |
| HindIII | 9.5 kb | 2.0 kb |
| EcoRI  | 1.6 kb | 3.6 kb |

Example 5

Absence of Other Vector DNA Sequences

To verify the absence of oriV, ori-322, aad and nptII sequences in the transformation event RRMax southern blot analysis can be performed using restriction enzyme/probe combinations covering oriV, ori-322, aad and nptII.

Transformation vector DNA is digested with restriction enzyme NspI which cuts the plasmid at 17 sites. For the purpose of the analysis a NspI fragment covering oriV and a fragment covering ori-322 and aad are purified and used for Southern Blot analysis. A PCR amplified fragment with the nucleotide sequence given in SEQ ID NO: 26 is used to probe for nptII sequences. All fragments are purified with the Geneclean II® Kit of BIO 101 (La Jolla, Calif.). Labelling with $^{32}P$ is achieved with the Megaprime™ DNA labelling system of Amersham International (Little Chalfont, UK).

Genomic DNA of RRMax is digested with the restriction enzyme BamHI which cuts the transformation vector DNA at three sites, positioned at basepairs 2321, 5544 and 8413 of SEQ ID NO: 5. Hybridization of the corresponding southern transfer membrane with the probe covering oriV failed to detect a signal. It has to be concluded that oriV is not present in RRMax.

Hybridization of the corresponding southern transfer membrane with the probe covering ori-322 and aad failed to detect a signal. It has to be concluded that ori-322 and aad sequences are not present in RRMax.

Hybridization of the corresponding southern transfer membrane with the nptII probe also failed to detect a signal, which demonstrates that an nptII gene is not present in line RRMax.

Example 6

Stability of the RRMax Line

Digestion of genomic DNA with the restriction enzyme BclI and Southern blot analysis using the cp4/epsps gene as a probe are performed as described in Example 2. Four plants from generations 2 and 3, and five plants from generation 4 are used for this analysis. In addition, 3 non-transgenic plants are used as a negative control. Analysis of the primary transformation event results in a single fragment of 3.2 kb. Southern blot analysis of the progeny generations also results in a single fragment of 3.2 kb. If the introduced DNA is stably inherited from generation to generation, the same fragment of 3.2 kb is expected in all plants.

Digestion of genomic DNA with HindIII and Southern blot analysis using an internal fragment of the gox gene as a probe are performed as described in Example 2. Analysis of the primary transformation event results in a single fragment of 2.0 kb. Southern blot analysis of the progeny generations also results in a single fragment of 2.0 kb indicating stable inheritance of the trait.

Example 7

PCR Characterization of RRMax

Genomic DNA of line RRMax is prepared as described in example 2. About 0.5 μg of DNA are used as template DNA in a PCR reaction using specific combinations of primers characterized by the sequences given in Table 6. Said specific combinations and the size of the fragment amplified are given in Table 7. Depending on the primer pair combination an annealing temperature between 55° C. and 65° C. is used in each of the 30 to 35 amplification cycles.

TABLE 6

Primer Sequences

| Primer | Sequence | | Description |
|---|---|---|---|
| A | 5'-TCAACCTACAGCTGATTTGGACCC-3' | (SEQ ID No: 17) | near the right border junction |
| B | 5'-GGACCGGAACGACAATCTGATC-3' | (SEQ ID No: 18) | near the right border junction |
| C | 5'-CTAGGGAAGTCCAAATCAGCCG-3' | (SEQ ID NO: 19) | near the left border junction |
| D | 5'-TTTGGACCGGAACTTTCCAGAAG-3' | (SEQ ID No: 20) | near the left border junction |
| a | 5'-CTAACTTGCGCCATCGGAGAAAC-3' | (SEQ ID No: 21) | within the cp4/epsps gene |
| b | 5'-GACTTGTCACCTGGAATACGGAC-3' | (SEQ ID No: 22) | within the cp4/epsps gene |
| c | 5'-ATTCTTGAGCTCATCAAGCAGCC-3' | (SEQ ID NO: 23) | within the cp4/epsps gene |
| e | 5'-AAGGTTGGTATCGCTGGAGCTG-3' | (SEQ ID No: 24) | within the gox sequences |
| f | 5'-TCTCCACAATGGCTTCCTCTATG-3' | (SEQ ID No: 25) | within the gox sequences |

TABLE 7

Specific Primer Combinations

| Combination | Size of amplified fragment |
|---|---|
| A + a | 757 bp |
| A + b | 1057 bp |
| A + c | 2352 bp |
| B + a | 739 bp (SEQ ID NO: 27) |
| B + b | 1039 bp |
| B + c | 2334 bp |
| C + e | 888 bp |
| C + f | 1224 bp |
| D + e | 834 bp |
| D + f | 1178 bp |

What is claimed is:

1. A glyphosate tolerant sugar beet plant, or parts thereof, seed of said sugar beet plant having been deposited with the National Collections of Industrial and Marine Bacteria Limited under Accession No. NCIMB 40905.

2. The glyphosate tolerant sugar beet plant of claim 1, or parts thereof, wherein DNA characterized by the nucleotide sequence of SEQ ID NO: 1 forms part of the plant's genome.

3. The glyphosate tolerant sugar beet plant of claim 1, or parts thereof, wherein DNA characterized by the nucleotide sequence of SEQ ID NO: 4 forms part of the plant's genome.

4. Descendants of the plant of claim 1, wherein DNA characterized by the nucleotide sequence of SEO ID NO:27 forms part of the plant's genome.

5. The plant of claim 4, wherein DNA characterized by the nucleotide sequence of SEQ ID NO:1 forms part of the plant's genome.

6. The plant of claim 5, wherein DNA characterized by the nucleotide sequence of SEQ ID NO:4 forms part of the plant's genome.

7. The plant of claim 4, wherein the parts of the genome directly linked to said nucleotide sequence are characterized by the nucleotide sequences of SEQ ID NO: 2 and SEQ ID NO: 3.

8. Seed of the glyphosate tolerant sugar beet plant of claims 1, 2, 3, 4, 5, 6, or 7.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
       (A) LENGTH: 8012 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 1:

```
AACGACAATC TGATCCCCAT CAAGCTTGAG CTCAGGATTT AGCAGCATTC CAGATTGGGT      60

TCAATCAACA AGGTACGAGC CATATCACTT TATTCAAATT GGTATCGCCA AAACCAAGAA     120

GGAACTCCCA TCCTCAAAGG TTTGTAAGGA AGAATTCTCA GTCCAAAGCC TCAACAAGGT     180

CAGGGTACAG AGTCTCCAAA CCATTAGCCA AAAGCTACAG GAGATCAATG AAGAATCTTC     240

AATCAAAGTA AACTACTGTT CCAGCACATG CATCATGGTC AGTAAGTTTC AGAAAAAGAC     300

ATCCACCGAA GACTTAAAGT TAGTGGGCAT CTTTGAAAGT AATCTTGTCA ACATCGAGCA     360

GCTGGCTTGT GGGGACCAGA CAAAAAAGGA ATGGTGCAGA ATTGTTAGGC GCACCTACCA     420

AAAGCATCTT TGCCTTTATT GCAAAGATAA AGCAGATTCC TCTAGTACAA GTGGGGAACA     480

AAATAACGTG GAAAGAGCT GTCCTGACAG CCCACTCACT AATGCGTATG ACGAACGCAG      540

TGACGACCAC AAAAGAATTC CCTCTATATA AGAAGGCATT CATTCCCATT TGAAGGATCA     600

TCAGATACTG AACCAATCCT TCTAGAAGAT CTAAGCTTAT CGATAAGCTT GATGTAATTG     660

GAGGAAGATC AAAATTTTCA ATCCCCATTC TTCGATTGCT TCAATTGAAG TTTCTCCGAT     720

GGCGCAAGTT AGCAGAATCT GCAATGGTGT GCAGAACCCA TCTCTTATCT CCAATCTCTC     780

GAAATCCAGT CAACGCAAAT CTCCCTTATC GGTTTCTCTG AAGACGCAGC AGCATCCACG     840

AGCTTATCCG ATTTCGTCGT CGTGGGGATT GAAGAAGAGT GGGATGACGT TAATTGGCTC     900

TGAGCTTCGT CCTCTTAAGG TCATGTCTTC TGTTTCCACG GCGTGCATGC TTCACGGTGC     960

AAGCAGCCGT CCAGCAACTG CTCGTAAGTC CTCTGGTCTT TCTGGAACCG TCCGTATTCC    1020

AGGTGACAAG TCTATCTCCC ACAGGTCCTT CATGTTTGGA GGTCTCGCTA GCGGTGAAAC    1080

TCGTATCACC GGTCTTTTGG AAGGTGAAGA TGTTATCAAC ACTGGTAAGG CTATGCAAGC    1140

TATGGGTGCC AGAATCCGTA AGGAAGGTGA TACTTGGATC ATTGATGGTG TTGGTAACGG    1200

TGGACTCCTT GCTCCTGAGG CTCCTCTCGA TTTCGGTAAC GCTGCAACTG GTTGCCGTTT    1260

GACTATGGGT CTTGTTGGTG TTTACGATTT CGATAGCACT TTCATTGGTG ACGCTTCTCT    1320

CACTAAGCGT CCAATGGGTC GTGTGTTGAA CCCACTTCGC GAAATGGGTG TGCAGGTGAA    1380

GTCTGAAGAC GGTGATCGTC TTCCAGTTAC CTTGCGTGGA CCAAAGACTC CAACGCCAAT    1440

CACCTACAGG GTACCTATGG CTTCCGCTCA AGTGAAGTCC GCTGTTCTGC TTGCTGGTCT    1500

CAACACCCCA GGTATCACCA CTGTTATCGA GCCAATCATG ACTCGTGACC ACACTGAAAA    1560

GATGCTTCAA GGTTTTGGTG CTAACCTTAC CGTTGAGACT GATGCTGACG GTGTGCGTAC    1620

CATCCGTCTT GAAGGTCGTG GTAAGCTCAC CGGTCAAGTG ATTGATGTTC CAGGTGATCC    1680
```

```
ATCCTCTACT GCTTTCCCAT TGGTTGCTGC CTTGCTTGTT CCAGGTTCCG ACGTCACCAT   1740

CCTTAACGTT TTGATGAACC CAACCCGTAC TGGTCTCATC TTGACTCTGC AGGAAATGGG   1800

TGCCGACATC GAAGTGATCA ACCCACGTCT TGCTGGTGGA AAGACGTGG  CTGACTTGCG   1860

TGTTCGTTCT TCTACTTTGA AGGGTGTTAC TGTTCCAGAA GACCGTGCTC CTTCTATGAT   1920

CGACGAGTAT CCAATTCTCG CTGTTGCAGC TGCATTCGCT GAAGGTGCTA CCGTTATGAA   1980

CGGTTTGGAA GAACTCCGTG TTAAGGAAAG CGACCGTCTT TCTGCTGTCG CAAACGGTCT   2040

CAAGCTCAAC GGTGTTGATT GCGATGAAGG TGAGACTTCT CTCGTCGTGC GTGGTCGTCC   2100

TGACGGTAAG GGTCTCGGTA ACGCTTCTGG AGCAGCTGTC GCTACCCACC TCGATCACCG   2160

TATCGCTATG AGCTTCCTCG TTATGGGTCT CGTTTCTGAA AACCCTGTTA CTGTTGATGA   2220

TGCTACTATG ATCGCTACTA GCTTCCCAGA GTTCATGGAT TTGATGGCTG GTCTTGGAGC   2280

TAAGATCGAA CTCTCCGACA CTAAGGCTGC TTGATGAGCT CAAGAATTCG AGCTCGGTAC   2340

CGGATCCTCT AGCTAGAGCT TTCGTTCGTA TCATCGGTTT CGACAACGTT CGTCAAGTTC   2400

AATGCATCAG TTTCATTGCG CACACACCAG AATCCTACTG AGTTCGAGTA TTATGGCATT   2460

GGGAAAACTG TTTTTCTTGT ACCATTTGTT GTGCTTGTAA TTTACTGTGT TTTTTATTCG   2520

GTTTTCGCTA TCGAACTGTG AAATGGAAAT GGATGGAGAA GAGTTAATGA ATGATATGGT   2580

CCTTTTGTTC ATTCTCAAAT TAATATTATT TGTTTTTTCT CTTATTTGTT GTGTGTTGAA   2640

TTTGAAATTA TAAGAGATAT GCAAACATTT TGTTTTGAGT AAAAATGTGT CAAATCGTGG   2700

CCTCTAATGA CCGAAGTTAA TATGAGGAGT AAAACACTTG TAGTTGTACC ATTATGCTTA   2760

TTCACTAGGC AACAAATATA TTTTCAGACC TAGAAAAGCT GCAAATGTTA CTGAATACAA   2820

GTATGTCCTC TTGTGTTTTA GACATTTATG AACTTTCCTT TATGTAATTT TCCAGAATCC   2880

TTGTCAGATT CTAATCATTG CTTTATAATT ATAGTTATAC TCATGGATTT GTAGTTGAGT   2940

ATGAAAATAT TTTTTAATGC ATTTTATGAC TTGCCAATTG ATTGACAACA TGCATCAATC   3000

GACCTGCAGC CACTCGAAGC GGCCGCGTTC AAGCTTCTGC AGGTCCGATG TGAGACTTTT   3060

CAACAAAGGG TAATATCCGG AAACCTCCTC GGATTCCATT GCCCAGCTAT CTGTCACTTT   3120

ATTGTGAAGA TAGTGGAAAA GGAAGGTGGC TCCTACAAAT GCCATCATTG CGATAAAGGA   3180

AAGGCCATCG TTGAAGATGC CTCTGCCGAC AGTGGTCCCA AGATGGACC  CCCACCCACG   3240

AGGAGCATCG TGGAAAAAGA AGACGTTCCA ACCACGTCTT CAAAGCAAGT GGATTGATGT   3300

GATGGTCCGA TGTGAGACTT TCAACAAAG  GGTAATATCC GGAAACCTCC TCGGATTCCA   3360

TTGCCCAGCT ATCTGTCACT TTATTGTGAA GATAGTGGAA AAGGAAGGTG GCTCCTACAA   3420

ATGCCATCAT TGCGATAAAG GAAAGGCCAT CGTTGAAGAT GCCTCTGCCG ACAGTGGTCC   3480

CAAAGATGGA CCCCCACCCA CGAGGAGCAT CGTGGAAAAA GAAGACGTTC AACCACGTC   3540

TTCAAAGCAA GTGGATTGAT GTGATATCTC CACTGACGTA AGGGATGACG CACAATCCCA   3600

CTATCCTTCG CAAGACCCTT CCTCTATATA AGGAAGTTCA TTTCATTTGG AGAGGACACG   3660

CTGACAAGCT GACTCTAGCA GATCTCCATG GTCCGTCCTG TAGAAACCCC AACCCGTGAA   3720

ATCAAAAAAC TCGACGGCCT GTGGGCATTC AGTCTGGATC GCGAAAACTG TGGAATTGAT   3780

CAGCGTTGGT GGGAAAGCGC GTTACAAGAA AGCCGGGCAA TTGCTGTGCC AGGCAGTTTT   3840

AACGATCAGT TCGCCGATGC AGATATTCGT AATTATGCGG GCAACGTCTG GTATCAGCGC   3900

GAAGTCTTTA TACCGAAAGG TTGGGCAGGC CAGCGTATCG TGCTGCGTTT CGATGCGGTC   3960

ACTCATTACG GCAAAGTGTG GGTCAATAAT CAGGAAGTGA TGGAGCATCA GGGCGGCTAT   4020
```

```
ACGCCATTTG AAGCCGATGT CACGCCGTAT GTTATTGCCG GGAAAAGTGT ACGTATCACC   4080

GTTTGTGTGA ACAACGAACT GAACTGGCAG ACTATCCCGC CGGGAATGGT GATTACCGAC   4140

GAAAACGGCA AGAAAAAGCA GTCTTACTTC CATGATTTCT TTAACTATGC CGGAATCCAT   4200

CGCAGCGTAA TGCTCTACAC CACGCCGAAC ACCTGGGTGG ACGATATCAC CGTGGTGACG   4260

CATGTCGCGC AAGACTGTAA CCACGCGTCT GTTGACTGGC AGGTGGTGGC CAATGGTGAT   4320

GTCAGCGTTG AACTGCGTGA TGCGGATCAA CAGGTGGTTG CAACTGGACA AGGCACTAGC   4380

GGGACTTTGC AAGTGGTGAA TCCGCACCTC TGGCAACCGG GTGAAGGTTA TCTCTATGAA   4440

CTGTGCGTCA CAGCCAAAAG CCAGACAGAG TGTGATATCT ACCCGCTTCG CGTCGGCATC   4500

CGGTCAGTGG CAGTGAAGGG CGAACAGTTC CTGATTAACC ACAAACCGTT CTACTTTACT   4560

GGCTTTGGTC GTCATGAAGA TGCGGACTTA CGTGGCAAAG GATTCGATAA CGTGCTGATG   4620

GTGCACGACC ACGCATTAAT GGACTGGATT GGGGCCAACT CCTACCGTAC CTCGCATTAC   4680

CCTTACGCTG AAGAGATGCT CGACTGGGCA GATGAACATG GCATCGTGGT GATTGATGAA   4740

ACTGCTGCTG TCGGCTTTAA CCTCTCTTTA GGCATTGGTT TCGAAGCGGG CAACAAGCCG   4800

AAAGAACTGT ACAGCGAAGA GGCAGTCAAC GGGGAAACTC AGCAAGCGCA CTTACAGGCG   4860

ATTAAAGAGC TGATAGCGCG TGACAAAAAC CACCCAAGCG TGGTGATGTG GAGTATTGCC   4920

AACGAACCGG ATACCCGTCC TGCACGGGAA TATTTCGGCA TTTCGCCACT GGCGGAAGCA   4980

ACGCGTAAAC TCGACCCGAC GCGTCCGATC ACCTGCGTCA ATGTAATGTT CTGCGACGCT   5040

CACACCGATA CCATCAGCGA TCTCTTTGAT GTGCTGTGCC TGAACCGTTA TTACGGATGG   5100

TATGTCCAAA GCGGCGATTT GGAAACGGCA GAGAAGGTAC TGGAAAAAGA ACTTCTGGCC   5160

TGGCAGGAGA AACTGCATCA GCCGATTATC ATCACCGAAT ACGGCGTGGA TACGTTAGCC   5220

GGGCTGCACT CAATGTACAC CGACATGTGG AGTGAAGAGT ATCAGTGTGC ATGGCTGGAT   5280

ATGTATCACC GCGTCTTTGA TCGCGTCAGC GCCGTCGTCG GTGAACAGGT ATGGAATTTC   5340

GCCGATTTTG CGACCTCGCA AGGCATATTG CGCGTTGGCG GTAACAAGAA AGGGATCTTC   5400

ACTCGCGACC GCAAACCGAA GTCGGCGGCT TTTCTGCTGC AAAAACGCTG GACTGGCATG   5460

AACTTCGGTG AAAAACCGCA GCAGGGAGGC AAACAATGAA TCAACAACTC TCCTGGCGCA   5520

CCATCGTCGG CTACAGCCTC GGTGGGAAT TCGAGCTCGC CCGGGGATCC TCTAGCTAGA   5580

GCTTTCGTTC GTATCATCGG TTTCGACAAC GTTCGTCAAG TTCAATGCAT CAGTTTCATT   5640

GCGCACACAC CAGAATCCTA CTGAGTTCGA GTATTATGGC ATTGGGAAAA CTGTTTTTCT   5700

TGTACCATTT GTTGTGCTTG TAATTTACTG TGTTTTTTAT TCGGTTTTCG CTATCGAACT   5760

GTGAAATGGA AATGGATGGA GAAGAGTTAA TGAATGATAT GGTCCTTTTG TTCATTCTCA   5820

AATTAATATT ATTTGTTTTT TCTCTTATTT GTTGTGTGTT GAATTTGAAA TTATAAGAGA   5880

TATGCAAACA TTTTGTTTTG AGTAAAAATG TGTCAAATCG TGGCCTCTAA TGACCGAAGT   5940

TAATATGAGG AGTAAAACAC TTGTAGTTGT ACCATTATGC TTATTCACTA GGCAACAAAT   6000

ATATTTTCAG ACCTAGAAAA GCTGCAAATG TTACTGAATA CAAGTATGTC CTCTTGTGTT   6060

TTAGACATTT ATGAACTTTC CTTTATGTAA TTTTCCAGAA TCCTTGTCAG ATTCTAATCA   6120

TTGCTTTATA ATTATAGTTA TACTCATGGA TTTGTAGTTG AGTATGAAAA TATTTTTTAA   6180

TGCATTTTAT GACTTGCCAA TTGATTGACA ACATGCATCA ATCGACCTGC AGCCCAAGCT   6240

TGAGCTCAGG ATTTAGCAGC ATTCCAGATT GGGTTCAATC AACAAGGTAC GAGCCATATC   6300

ACTTTATTCA AATTGGTATC GCCAAAACCA AGAAGGAACT CCCATCCTCA AAGGTTTGTA   6360

AGGAAGAATT CTCAGTCCAA AGCCTCAACA AGGTCAGGGT ACAGAGTCTC CAAACCATTA   6420
```

-continued

```
GCCAAAAGCT ACAGGAGATC AATGAAGAAT CTTCAATCAA AGTAAACTAC TGTTCCAGCA      6480

CATGCATCAT GGTCAGTAAG TTTCAGAAAA AGACATCCAC CGAAGACTTA AAGTTAGTGG      6540

GCATCTTTGA AAGTAATCTT GTCAACATCG AGCAGCTGGC TTGTGGGGAC CAGACAAAAA      6600

AGGAATGGTG CAGAATTGTT AGGCGCACCT ACCAAAAGCA TCTTTGCCTT TATTGCAAAG      6660

ATAAAGCAGA TTCCTCTAGT ACAAGTGGGG AACAAAATAA CGTGGAAAAG AGCTGTCCTG      6720

ACAGCCCACT CACTAATGCG TATGACGAAC GCAGTGACGA CCACAAAAGA ATTCCCTCTA      6780

TATAAGAAGG CATTCATTCC CATTTGAAGG ATCATCAGAT ACTGAACCAA TCCTTCTAGA      6840

AGATCTCCAC AATGGCTTCC TCTATGCTCT CTTCCGCTAC TATGGTTGCC TCTCCGGCTC      6900

AGGCCACTAT GGTCGCTCCT TTCAACGGAC TTAAGTCCTC CGCTGCCTTC CCAGCCACCC      6960

GCAAGGCTAA AACGACATT ACTTCCATCA AAGCAACGG CGGAAGAGTT AACTGCATGC        7020

AGGTGTGGCC TCCGATTGGA AAGAAGAAGT TTGAGACTCT CTCTTACCTT CCTGACCTTA      7080

CCGATTCCGG TGGTCGCGTC AACTGCATGC AGGCCATGGC TGAGAACCAC AAGAAGGTTG      7140

GTATCGCTGG AGCTGGAATC GTTGGTGTTT GCACTGCTTT GATGCTTCAA CGTCGTGGAT      7200

TCAAGGTTAC CTTGATTGAT CCAAACCCAC CAGGTGAAGG TGCTTCTTTC GGTAACGCTG      7260

GTTGCTTCAA CGGTTCCTCC GTTGTTCCAA TGTCCATGCC AGGAAACTTG ACTAGCGTTC      7320

CAAAGTGGCT TCTTGACCCA ATGGGTCCAT TGTCCATCCG TTTCAGCTAC TTTCCAACCA      7380

TCATGCCTTG GTTGATTCGT TTCTTGCTTG CTGGAAGACC AAACAAGGTG AAGGAGCAAG      7440

CTAAGGCACT CCGTAACCTC ATCAAGTCCA CTGTGCCTTT GATCAAGTCC TTGGCTGAGG      7500

AGGCTGATGC TAGCCACCTT ATCCGTCACG AAGGTCACCT TACCGTGTAC CGTGGAGAAG      7560

CAGACTTCGC CAAGGACCGT GGAGGTTGGG AACTTCGTCG TCTCAACGGT GTTCGTACTC      7620

AAATCCTCAG CGCTGATGCA TTGCGTGATT TCGATCCTAA CTTGTCTCAC GCCTTTACCA      7680

AGGGAATCCT TATCGAAGAG AACGGTCACA CCATCAACCC ACAAGGTCTC GTGACTCTCT      7740

TGTTTCGTCG TTTCATCGCT AACGGTGGAG AGTTCGTGTC TGCTCGTGTT ATCGGATTCG      7800

AGACTGAAGG TCGTGCTCTC AAGGGTATCA CCACCACCAA CGGTGTTCTT GCTGTTGATG      7860

CAGCTGTTGT TGCAGCTGGT GCACACTCCA AGTCTCTTGC TAACTCCCTT GGTGATGACA      7920

TCCCATTGGA TACCGAACGT GGATACCACA TCGTGATCGC CAACCCAGAA GCTGCTCCAC      7980

GTATTCCAAC TACCGATGCT TCTGGAAAGT TC                                   8012
```

(2) INFORMATION FOR SEQ ID NO: 2:

(i) SEQUENCE CHARACTERISTICS:
        (A) LENGTH: 89 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 2:

```
GGATTGTGTT TGGGTTTTGT CTGTGTGTTT AATGTGTTTA AGGGATGAAT TAGAATGCTC       60
TTAATCAACC TACAGCTGAT TTGGACCGG                                        89
```

(2) INFORMATION FOR SEQ ID NO: 3:

(i) SEQUENCE CHARACTERISTICS:
    (A) LENGTH: 697 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 3:

```
CGGTCCAAAT TGTTTACAT TGTGTCCAAA TTTCGGCTGA TTTGGACTTC CCTAGCTATG      60

CCAACTAAGC TAATAAAAAA CATGAAACAA CAATTACAAA CTGTCGAGCA CACCTTCTAC    120

AAACTAGCTT AGATTTCTAT TGGAAGTTAC AAAACAGTAA AACTACCAAT AGGATACTAA    180

ATTAAACATA TTAAACTATT ACTCCTCAAA AGCTTGTACA ATTTGCAGAA GAAATGATGG    240

TTGCCCAAAA GCTTCAAAGG GAACCTGCTG GGAAGCCTGC TGGGACGCTG GGGATGCTGG    300

CAGCAGCATA CCTTGGCTTG AAGTACTCTT CTCTCATTGG TTTTGCTTCC CTTGCCCATG    360

TGGTCTTCAT ATGGCCTCAT TACTTCCCAA GGGCTTCAAA TCAGTAGGTG GTGGCAACCA    420

AAAGCATCAA AAACATCTCC TAAAACTAGC TTATACAACC GGATTACATG AGCTTATACT    480

AGCTTAACTC TTAAAGCATG ATTAACATAA TGATGTTTAA GGTGTCATTA AGTATTACTA    540

ATCTTGCTTA AGTAGAGATT AACATAGGAT TAGCCTAATC AAGTTGCTTA AGTAAGGTTT    600

TAGAATAAAC CGAGCTAGTT AGGCTTAAGT AGAGATTAAC ATAGGATTAG CCTAATCAAG    660

TTGCTTAAGT AAGGTTTTAG AATAAACCGA GCTAGTT                             697
```

(2) INFORMATION FOR SEQ ID NO: 4:

(i) SEQUENCE CHARACTERISTICS:
        (A) LENGTH: 8798 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 4:

```
GGATTGTGTT TGGGTTTTGT CTGTGTGTTT AATGTGTTTA AGGGATGAAT TAGAATGCTC     60

TTAATCAACC TACAGCTGAT TTGGACCGGA ACGACAATCT GATCCCCATC AAGCTTGAGC    120

TCAGGATTTA GCAGCATTCC AGATTGGGTT CAATCAACAA GGTACGAGCC ATATCACTTT    180

ATTCAAATTG GTATCGCCAA AACCAAGAAG GAACTCCCAT CCTCAAAGGT TTGTAAGGAA    240

GAATTCTCAG TCCAAAGCCT CAACAAGGTC AGGGTACAGA GTCTCCAAAC CATTAGCCAA    300

AAGCTACAGG AGATCAATGA AGAATCTTCA ATCAAAGTAA ACTACTGTTC CAGCACATGC    360

ATCATGGTCA GTAAGTTTCA GAAAAAGACA TCCACCGAAG ACTTAAAGTT AGTGGGCATC    420

TTTGAAAGTA ATCTTGTCAA CATCGAGCAG CTGGCTTGTG GGACCAGAC AAAAAAGGAA    480

TGGTGCAGAA TTGTTAGGCG CACCTACCAA AAGCATCTTT GCCTTTATTG CAAAGATAAA    540

GCAGATTCCT CTAGTACAAG TGGGAACAA ATAACGTGG AAAAGAGCTG TCCTGACAGC    600

CCACTCACTA ATGCGTATGA CGAACGCAGT GACGACCACA AAAGAATTCC CTCTATATAA    660

GAAGGCATTC ATTCCCATTT GAAGGATCAT CAGATACTGA ACCAATCCTT CTAGAAGATC    720
```

```
TAAGCTTATC GATAAGCTTG ATGTAATTGG AGGAAGATCA AAATTTTCAA TCCCCATTCT      780

TCGATTGCTT CAATTGAAGT TTCTCCGATG GCGCAAGTTA GCAGAATCTG CAATGGTGTG      840

CAGAACCCAT CTCTTATCTC CAATCTCTCG AAATCCAGTC AACGCAAATC TCCCTTATCG      900

GTTTCTCTGA AGACGCAGCA GCATCCACGA GCTTATCCGA TTTCGTCGTC GTGGGATTG       960

AAGAAGAGTG GGATGACGTT AATTGGCTCT GAGCTTCGTC CTCTTAAGGT CATGTCTTCT     1020

GTTTCCACGG CGTGCATGCT TCACGGTGCA AGCAGCCGTC CAGCAACTGC TCGTAAGTCC     1080

TCTGGTCTTT CTGGAACCGT CCGTATTCCA GGTGACAAGT CTATCTCCCA CAGGTCCTTC     1140

ATGTTTGGAG GTCTCGCTAG CGGTGAAACT CGTATCACCG GTCTTTTGGA AGGTGAAGAT     1200

GTTATCAACA CTGGTAAGGC TATGCAAGCT ATGGGTGCCA GAATCCGTAA GGAAGGTGAT     1260

ACTTGGATCA TTGATGGTGT TGGTAACGGT GGACTCCTTG CTCCTGAGGC TCCTCTCGAT     1320

TTCGGTAACG CTGCAACTGG TTGCCGTTTG ACTATGGGTC TTGTTGGTGT TTACGATTTC     1380

GATAGCACTT TCATTGGTGA CGCTTCTCTC ACTAAGCGTC CAATGGGTCG TGTGTTGAAC     1440

CCACTTCGCG AAATGGGTGT GCAGGTGAAG TCTGAAGACG GTGATCGTCT TCCAGTTACC     1500

TTGCGTGGAC CAAAGACTCC AACGCCAATC ACCTACAGGG TACCTATGGC TTCCGCTCAA     1560

GTGAAGTCCG CTGTTCTGCT TGCTGGTCTC AACACCCCAG GTATCACCAC TGTTATCGAG     1620

CCAATCATGA CTCGTGACCA CACTGAAAAG ATGCTTCAAG GTTTTGGTGC TAACCTTACC     1680

GTTGAGACTG ATGCTGACGG TGTGCGTACC ATCCGTCTTG AAGGTCGTGG TAAGCTCACC     1740

GGTCAAGTGA TTGATGTTCC AGGTGATCCA TCCTCTACTG CTTTCCCATT GGTTGCTGCC     1800

TTGCTTGTTC CAGGTTCCGA CGTCACCATC CTTAACGTTT TGATGAACCC AACCCGTACT     1860

GGTCTCATCT TGACTCTGCA GGAAATGGGT GCCGACATCA AGTGATCAA CCCACGTCTT     1920

GCTGGTGGAG AAGACGTGGC TGACTTGCGT GTTCGTTCTT CTACTTTGAA GGGTGTTACT     1980

GTTCCAGAAG ACCGTGCTCC TTCTATGATC GACGAGTATC CAATTCTCGC TGTTGCAGCT     2040

GCATTCGCTG AAGGTGCTAC CGTTATGAAC GGTTTGGAAG AACTCCGTGT TAAGGAAAGC     2100

GACCGTCTTT CTGCTGTCGC AAACGGTCTC AAGCTCAACG GTGTTGATTG CGATGAAGGT     2160

GAGACTTCTC TCGTCGTGCG TGGTCGTCCT GACGGTAAGG GTCTCGGTAA CGCTTCTGGA     2220

GCAGCTGTCG CTACCCACCT CGATCACCGT ATCGCTATGA GCTTCCTCGT TATGGGTCTC     2280

GTTTCTGAAA ACCCTGTTAC TGTTGATGAT GCTACTATGA TCGCTACTAG CTTCCCAGAG     2340

TTCATGGATT TGATGGCTGG TCTTGGAGCT AAGATCGAAC TCTCCGACAC TAAGGCTGCT     2400

TGATGAGCTC AAGAATTCGA GCTCGGTACC GGATCCTCTA GCTAGAGCTT CGTTCGTAT     2460

CATCGGTTTC GACAACGTTC GTCAAGTTCA ATGCATCAGT TCATTGCGC ACACACCAGA     2520

ATCCTACTGA GTTCGAGTAT TATGGCATTG GGAAAACTGT TTTTCTTGTA CCATTTGTTG     2580

TGCTTGTAAT TTACTGTGTT TTTTATTCGG TTTTCGCTAT CGAACTGTGA AATGGAAATG     2640

GATGGAGAAG AGTTAATGAA TGATATGGTC CTTTTGTTCA TTCTCAAATT AATATTATTT     2700

GTTTTTTCTC TTATTTGTTG TGTGTTGAAT TTGAAATTAT AAGAGATATG CAAACATTTT     2760

GTTTTGAGTA AAAATGTGTC AAATCGTGGC CTCTAATGAC CGAAGTTAAT ATGAGGAGTA     2820

AAACACTTGT AGTTGTACCA TTATGCTTAT TCACTAGGCA ACAAATATAT TTCAGACCT      2880

AGAAAAGCTG CAAATGTTAC TGAATACAAG TATGTCCTCT TGTGTTTTAG ACATTTATGA     2940

ACTTTCCTTT ATGTAATTTT CCAGAATCCT TGTCAGATTC TAATCATTGC TTTATAATTA     3000

TAGTTATACT CATGGATTTG TAGTTGAGTA TGAAAATATT TTTAATGCA TTTTATGACT     3060

TGCCAATTGA TTGACAACAT GCATCAATCG ACCTGCAGCC ACTCGAAGCG GCCGCGTTCA     3120
```

-continued

```
AGCTTCTGCA GGTCCGATGT GAGACTTTTC AACAAAGGGT AATATCCGGA AACCTCCTCG    3180
GATTCCATTG CCCAGCTATC TGTCACTTTA TTGTGAAGAT AGTGGAAAAG GAAGGTGGCT    3240
CCTACAAATG CCATCATTGC GATAAAGGAA AGGCCATCGT TGAAGATGCC TCTGCCGACA    3300
GTGGTCCCAA AGATGGACCC CCACCCACGA GGAGCATCGT GGAAAAAGAA GACGTTCCAA    3360
CCACGTCTTC AAAGCAAGTG GATTGATGTG ATGGTCCGAT GTGAGACTTT TCAACAAAGG    3420
GTAATATCCG GAAACCTCCT CGGATTCCAT TGCCCAGCTA TCTGTCACTT TATTGTGAAG    3480
ATAGTGGAAA AGGAAGGTGG CTCCTACAAA TGCCATCATT GCGATAAAGG AAAGGCCATC    3540
GTTGAAGATG CCTCTGCCGA CAGTGGTCCC AAAGATGGAC CCCCACCCAC GAGGAGCATC    3600
GTGGAAAAAG AAGACGTTCC AACCACGTCT TCAAAGCAAG TGGATTGATG TGATATCTCC    3660
ACTGACGTAA GGGATGACGC ACAATCCCAC TATCCTTCGC AAGACCCTTC CTCTATATAA    3720
GGAAGTTCAT TCATTTGGA GAGGACACGC TGACAAGCTG ACTCTAGCAG ATCTCCATGG     3780
TCCGTCCTGT AGAAACCCCA ACCCGTGAAA TCAAAAAACT CGACGGCCTG TGGGCATTCA    3840
GTCTGGATCG CGAAAACTGT GGAATTGATC AGCGTTGGTG GGAAAGCGCG TTACAAGAAA    3900
GCCGGGCAAT TGCTGTGCCA GGCAGTTTTA ACGATCAGTT CGCCGATGCA GATATTCGTA    3960
ATTATGCGGG CAACGTCTGG TATCAGCGCG AAGTCTTTAT ACCGAAAGGT TGGGCAGGCC    4020
AGCGTATCGT GCTGCGTTTC GATGCGGTCA CTCATTACGG CAAAGTGTGG GTCAATAATC    4080
AGGAAGTGAT GGAGCATCAG GGCGGCTATA CGCCATTTGA AGCCGATGTC ACGCCGTATG    4140
TTATTGCCGG GAAAAGTGTA CGTATCACCG TTTGTGTGAA CAACGAACTG AACTGGCAGA    4200
CTATCCCGCC GGGAATGGTG ATTACCGACG AAAACGGCAA GAAAAAGCAG TCTTACTTCC    4260
ATGATTTCTT TAACTATGCC GGAATCCATC GCAGCGTAAT GCTCTACACC ACGCCGAACA    4320
CCTGGGTGGA CGATATCACC GTGGTGACGC ATGTCGCGCA AGACTGTAAC CACGCGTCTG    4380
TTGACTGGCA GGTGGTGGCC AATGGTGATG TCAGCGTTGA ACTGCGTGAT GCGGATCAAC    4440
AGGTGGTTGC AACTGGACAA GGCACTAGCG GGACTTTGCA AGTGGTGAAT CCGCACCTCT    4500
GGCAACCGGG TGAAGGTTAT CTCTATGAAC TGTGCGTCAC AGCCAAAAGC CAGACAGAGT    4560
GTGATATCTA CCCGCTTCGC GTCGGCATCC GGTCAGTGGC AGTGAAGGGC GAACAGTTCC    4620
TGATTAACCA CAAACCGTTC TACTTTACTG GCTTTGGTCG TCATGAAGAT GCGGACTTAC    4680
GTGGCAAAGG ATTCGATAAC GTGCTGATGG TGCACGACCA CGCATTAATG GACTGGATTG    4740
GGGCCAACTC CTACCGTACC TCGCATTACC CTTACGCTGA AGAGATGCTC GACTGGGCAG    4800
ATGAACATGG CATCGTGGTG ATTGATGAAA CTGCTGCTGT CGGCTTTAAC CTCTCTTTAG    4860
GCATTGGTTT CGAAGCGGGC AACAAGCCGA AGAACTGTA CAGCGAAGAG GCAGTCAACG     4920
GGGAAACTCA GCAAGCGCAC TTACAGGCGA TTAAAGAGCT GATAGCGCGT GACAAAAACC    4980
ACCCAAGCGT GGTGATGTGG AGTATTGCCA ACGAACCGGA TACCCGTCCT GCACGGGAAT    5040
ATTTCGGCAT TTCGCCACTG GCGGAAGCAA CGCGTAAACT CGACCCGACG CGTCCGATCA    5100
CCTGCGTCAA TGTAATGTTC TGCGACGCTC ACACCGATAC CATCAGCGAT CTCTTTGATG    5160
TGCTGTGCCT GAACCGTTAT TACGGATGGT ATGTCCAAAG CGGCGATTTG GAAACGGCAG    5220
AGAAGGTACT GGAAAAAGAA CTTCTGGCCT GGCAGGAGAA ACTGCATCAG CCGATTATCA    5280
TCACCGAATA CGGCGTGGAT ACGTTAGCCG GGCTGCACTC AATGTACACC GACATGTGGA    5340
GTGAAGAGTA TCAGTGTGCA TGGCTGGATA TGTATCACCG CGTCTTTGAT CGCGTCAGCG    5400
CCGTCGTCGG TGAACAGGTA TGGAATTTCG CCGATTTTGC GACCTCGCAA GGCATATTGC    5460
```

-continued

```
GCGTTGGCGG TAACAAGAAA GGGATCTTCA CTCGCGACCG CAAACCGAAG TCGGCGGCTT    5520

TTCTGCTGCA AAAACGCTGG ACTGGCATGA ACTTCGGTGA AAAACCGCAG CAGGGAGGCA    5580

AACAATGAAT CAACAACTCT CCTGGCGCAC CATCGTCGGC TACAGCCTCG GTGGGGAATT    5640

CGAGCTCGCC CGGGGATCCT CTAGCTAGAG CTTTCGTTCG TATCATCGGT TTCGACAACG    5700

TTCGTCAAGT TCAATGCATC AGTTTCATTG CGCACACACC AGAATCCTAC TGAGTTCGAG    5760

TATTATGGCA TTGGGAAAAC TGTTTTTCTT GTACCATTTG TTGTGCTTGT AATTTACTGT    5820

GTTTTTTATT CGGTTTTCGC TATCGAACTG TGAAATGGAA ATGGATGGAG AAGAGTTAAT    5880

GAATGATATG GTCCTTTTGT TCATTCTCAA ATTAATATTA TTTGTTTTTT CTCTTATTTG    5940

TTGTGTGTTG AATTTGAAAT TATAAGAGAT ATGCAAACAT TTTGTTTTGA GTAAAAATGT    6000

GTCAAATCGT GGCCTCTAAT GACCGAAGTT AATATGAGGA GTAAAACACT TGTAGTTGTA    6060

CCATTATGCT TATTCACTAG GCAACAAATA TATTTTCAGA CCTAGAAAAG CTGCAAATGT    6120

TACTGAATAC AAGTATGTCC TCTTGTGTTT TAGACATTTA TGAACTTTCC TTTATGTAAT    6180

TTTCCAGAAT CCTTGTCAGA TTCTAATCAT TGCTTTATAA TTATAGTTAT ACTCATGGAT    6240

TTGTAGTTGA GTATGAAAAT ATTTTTTAAT GCATTTTATG ACTTGCCAAT TGATTGACAA    6300

CATGCATCAA TCGACCTGCA GCCCAAGCTT GAGCTCAGGA TTTAGCAGCA TTCCAGATTG    6360

GGTTCAATCA ACAAGGTACG AGCCATATCA CTTTATTCAA ATTGGTATCG CCAAAACCAA    6420

GAAGGAACTC CCATCCTCAA AGGTTTGTAA GGAAGAATTC TCAGTCCAAA GCCTCAACAA    6480

GGTCAGGGTA CAGAGTCTCC AAACCATTAG CCAAAAGCTA CAGGAGATCA ATGAAGAATC    6540

TTCAATCAAA GTAAACTACT GTTCCAGCAC ATGCATCATG GTCAGTAAGT TTCAGAAAAA    6600

GACATCCACC GAAGACTTAA AGTTAGTGGG CATCTTTGAA AGTAATCTTG TCAACATCGA    6660

GCAGCTGGCT TGTGGGGACC AGACAAAAAA GGAATGGTGC AGAATTGTTA GGCGCACCTA    6720

CCAAAAGCAT CTTTGCCTTT ATTGCAAAGA TAAAGCAGAT TCCTCTAGTA CAAGTGGGGA    6780

ACAAAATAAC GTGGAAAAGA GCTGTCCTGA CAGCCCACTC ACTAATGCGT ATGACGAACG    6840

CAGTGACGAC CACAAAAGAA TTCCCTCTAT ATAAGAAGGC ATTCATTCCC ATTTGAAGGA    6900

TCATCAGATA CTGAACCAAT CCTTCTAGAA GATCTCCACA ATGGCTTCCT CTATGCTCTC    6960

TTCCGCTACT ATGGTTGCCT CTCCGGCTCA GGCCACTATG GTCGCTCCTT TCAACGGACT    7020

TAAGTCCTCC GCTGCCTTCC CAGCCACCCG CAAGGCTAAC AACGACATTA CTTCCATCAC    7080

AAGCAACGGC GGAAGAGTTA ACTGCATGCA GGTGTGGCCT CCGATTGGAA AGAAGAAGTT    7140

TGAGACTCTC TCTTACCTTC CTGACCTTAC CGATTCCGGT GGTCGCGTCA ACTGCATGCA    7200

GGCCATGGCT GAGAACCACA AGAAGGTTGG TATCGCTGGA GCTGGAATCG TTGGTGTTTG    7260

CACTGCTTTG ATGCTTCAAC GTCGTGGATT CAAGGTTACC TTGATTGATC AAACCCACC    7320

AGGTGAAGGT GCTTCTTTCG GTAACGCTGG TTGCTTCAAC GGTTCCTCCG TTGTTCCAAT    7380

GTCCATGCCA GGAAACTTGA CTAGCGTTCC AAAGTGGCTT CTTGACCCAA TGGGTCCATT    7440

GTCCATCCGT TTCAGCTACT TTCCAACCAT CATGCCTTGG TTGATTCGTT TCTTGCTTGC    7500

TGGAAGACCA AACAAGGTGA AGGAGCAAGC TAAGGCACTC CGTAACCTCA TCAAGTCCAC    7560

TGTGCCTTTG ATCAAGTCCT TGGCTGAGGA GGCTGATGCT AGCCACCTTA CCGTCACGA    7620

AGGTCACCTT ACCGTGTACC GTGGAGAAGC AGACTTCGCC AAGGACGTG GAGGTTGGGA    7680

ACTTCGTCGT CTCAACGGTG TTCGTACTCA AATCCTCAGC GCTGATGCAT TGCGTGATTT    7740

CGATCCTAAC TTGTCTCACG CCTTTACCAA GGGAATCCTT ATCGAAGAGA ACGGTCACAC    7800

CATCAACCCA CAAGGTCTCG TGACTCTCTT GTTTCGTCGT TTCATCGCTA ACGGTGGAGA    7860
```

```
GTTCGTGTCT GCTCGTGTTA TCGGATTCGA GACTGAAGGT CGTGCTCTCA AGGGTATCAC    7920

CACCACCAAC GGTGTTCTTG CTGTTGATGC AGCTGTTGTT GCAGCTGGTG CACACTCCAA    7980

GTCTCTTGCT AACTCCCTTG GTGATGACAT CCCATTGGAT ACCGAACGTG GATACCACAT    8040

CGTGATCGCC AACCCAGAAG CTGCTCCACG TATTCCAACT ACCGATGCTT CTGGAAAGTT    8100

CCGGTCCAAA TTTGTTTACA TTGTGTCCAA ATTTCGGCTG ATTTGGACTT CCCTAGCTAT    8160

GCCAACTAAG CTAATAAAAA ACATGAAACA ACAATTACAA ACTGTCGAGC ACACCTTCTA    8220

CAAACTAGCT TAGATTTCTA TTGGAAGTTA CAAAACAGTA AAACTACCAA TAGGATACTA    8280

AATTAAACAT ATTAAACTAT TACTCCTCAA AAGCTTGTAC AATTTGCAGA AGAAATGATG    8340

GTTGCCCAAA AGCTTCAAAG GGAACCTGCT GGGAAGCCTG CTGGGACGCT GGGGATGCTG    8400

GCAGCAGCAT ACCTTGGCTT GAAGTACTCT TCTCTCATTG GTTTTGCTTC CCTTGCCCAT    8460

GTGGTCTTCA TATGGCCTCA TTACTTCCCA AGGGCTTCAA ATCAGTAGGT GGTGGCAACC    8520

AAAAGCATCA AAACATCTC CTAAAACTAG CTTATACAAC CGGATTACAT GAGCTTATAC    8580

TAGCTTAACT CTTAAAGCAT GATTAACATA ATGATGTTTA AGGTGTCATT AAGTATTACT    8640

AATCTTGCTT AAGTAGAGAT TAACATAGGA TTAGCCTAAT CAAGTTGCTT AAGTAAGGTT    8700

TTAGAATAAA CCGAGCTAGT TAGGCTTAAG TAGAGATTAA CATAGGATTA GCCTAATCAA    8760

GTTGCTTAAG TAAGGTTTTA GAATAAACCG AGCTAGTT                            8798

(2) INFORMATION FOR SEQ ID NO: 5:

(i) SEQUENCE CHARACTERISTICS:
        (A) LENGTH: 8418 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 5:

AAGCTTGAGC TCAGGATTTA GCAGCATTCC AGATTGGGTT CAATCAACAA GGTACGAGCC      60

ATATCACTTT ATTCAAATTG GTATCGCCAA AACCAAGAAG GAACTCCCAT CCTCAAAGGT     120

TTGTAAGGAA GAATTCTCAG TCCAAAGCCT CAACAAGGTC AGGGTACAGA GTCTCCAAAC     180

CATTAGCCAA AAGCTACAGG AGATCAATGA AGAATCTTCA ATCAAAGTAA ACTACTGTTC     240

CAGCACATGC ATCATGGTCA GTAAGTTTCA GAAAAAGACA TCCACCGAAG ACTTAAAGTT     300

AGTGGGCATC TTTGAAAGTA ATCTTGTCAA CATCGAGCAG CTGGCTTGTG GGACCAGAC     360

AAAAAAGGAA TGGTGCAGAA TTGTTAGGCG CACCTACCAA AAGCATCTTT GCCTTTATTG     420

CAAAGATAAA GCAGATTCCT CTAGTACAAG TGGGAACAA AATAACGTGG AAAAGAGCTG     480

TCCTGACAGC CCACTCACTA ATGCGTATGA CGAACGCAGT GACGACCACA AAAGAATTCC     540

CTCTATATAA GAAGGCATTC ATTCCCATTT GAAGGATCAT CAGATACTGA ACCAATCCTT     600

CTAGAAGATC TAAGCTTATC GATAAGCTTG ATGTAATTGG AGGAAGATCA AAATTTTCAA     660

TCCCCATTCT TCGATTGCTT CAATTGAAGT TTCTCCGATG GCGCAAGTTA GCAGAATCTG     720

CAATGGTGTG CAGAACCCAT CTCTTATCTC CAATCTCTCG AAATCCAGTC AACGCAAATC     780

TCCCTTATCG GTTTCTCTGA AGACGCAGCA GCATCCACGA GCTTATCCGA TTTCGTCGTC     840

GTGGGGATTG AAGAAGAGTG GGATGACGTT AATTGGCTCT GAGCTTCGTC CTCTTAAGGT     900
```

```
CATGTCTTCT GTTTCCACGG CGTGCATGCT TCACGGTGCA AGCAGCCGTC CAGCAACTGC    960

TCGTAAGTCC TCTGGTCTTT CTGGAACCGT CCGTATTCCA GGTGACAAGT CTATCTCCCA   1020

CAGGTCCTTC ATGTTTGGAG GTCTCGCTAG CGGTGAAACT CGTATCACCG GTCTTTTGGA   1080

AGGTGAAGAT GTTATCAACA CTGGTAAGGC TATGCAAGCT ATGGGTGCCA GAATCCGTAA   1140

GGAAGGTGAT ACTTGGATCA TTGATGGTGT TGGTAACGGT GGACTCCTTG CTCCTGAGGC   1200

TCCTCTCGAT TTCGGTAACG CTGCAACTGG TTGCCGTTTG ACTATGGGTC TTGTTGGTGT   1260

TTACGATTTC GATAGCACTT TCATTGGTGA CGCTTCTCTC ACTAAGCGTC AATGGGTCG    1320

TGTGTTGAAC CCACTTCGCG AAATGGGTGT GCAGGTGAAG TCTGAAGACG GTGATCGTCT   1380

TCCAGTTACC TTGCGTGGAC CAAAGACTCC AACGCCAATC ACCTACAGGG TACCTATGGC   1440

TTCCGCTCAA GTGAAGTCCG CTGTTCTGCT TGCTGGTCTC AACACCCCAG GTATCACCAC   1500

TGTTATCGAG CCAATCATGA CTCGTGACCA CACTGAAAAG ATGCTTCAAG GTTTTGGTGC   1560

TAACCTTACC GTTGAGACTG ATGCTGACGG TGTGCGTACC ATCCGTCTTG AAGGTCGTGG   1620

TAAGCTCACC GGTCAAGTGA TTGATGTTCC AGGTGATCCA TCCTCTACTG CTTTCCCATT   1680

GGTTGCTGCC TTGCTTGTTC CAGGTTCCGA CGTCACCATC CTTAACGTTT TGATGAACCC   1740

AACCCGTACT GGTCTCATCT TGACTCTGCA GGAAATGGGT GCCGACATCG AAGTGATCAA   1800

CCCACGTCTT GCTGGTGGAG AAGACGTGGC TGACTTGCGT GTTCGTTCTT CTACTTTGAA   1860

GGGTGTTACT GTTCCAGAAG ACCGTGCTCC TTCTATGATC GACGAGTATC CAATTCTCGC   1920

TGTTGCAGCT GCATTCGCTG AAGGTGCTAC CGTTATGAAC GGTTTGGAAG AACTCCGTGT   1980

TAAGGAAAGC GACCGTCTTT CTGCTGTCGC AAACGGTCTC AAGCTCAACG GTGTTGATTG   2040

CGATGAAGGT GAGACTTCTC TCGTCGTGCG TGGTCGTCCT GACGGTAAGG GTCTCGGTAA   2100

CGCTTCTGGA GCAGCTGTCG CTACCCACCT CGATCACCGT ATCGCTATGA GCTTCCTCGT   2160

TATGGGTCTC GTTTCTGAAA ACCCTGTTAC TGTTGATGAT GCTACTATGA TCGCTACTAG   2220

CTTCCCAGAG TTCATGGATT TGATGGCTGG TCTTGGAGCT AAGATCGAAC TCTCCGACAC   2280

TAAGGCTGCT TGATGAGCTC AAGAATTCGA GCTCGGTACC GGATCCTCTA GCTAGAGCTT   2340

TCGTTCGTAT CATCGGTTTC GACAACGTTC GTCAAGTTCA ATGCATCAGT TTCATTGCGC   2400

ACACACCAGA ATCCTACTGA GTTCGAGTAT TATGGCATTG GGAAAACTGT TTTTCTTGTA   2460

CCATTTGTTG TGCTTGTAAT TTACTGTGTT TTTTATTCGG TTTTCGCTAT CGAACTGTGA   2520

AATGGAAATG GATGGAGAAG AGTTAATGAA TGATATGGTC CTTTTGTTCA TTCTCAAATT   2580

AATATTATTT GTTTTTTCTC TTATTTGTTG TGTGTTGAAT TGAAATTAT AAGAGATATG    2640

CAAACATTTT GTTTTGAGTA AAAATGTGTC AAATCGTGGC CTCTAATGAC CGAAGTTAAT   2700

ATGAGGAGTA AAACACTTGT AGTTGTACCA TTATGCTTAT TCACTAGGCA ACAAATATAT   2760

TTTCAGACCT AGAAAAGCTG CAAATGTTAC TGAATACAAG TATGTCCTCT TGTGTTTTAG   2820

ACATTTATGA ACTTTCCTTT ATGTAATTTT CCAGAATCCT TGTCAGATTC TAATCATTGC   2880

TTTATAATTA TAGTTATACT CATGGATTTG TAGTTGAGTA TGAAAATATT TTTTAATGCA   2940

TTTTATGACT TGCCAATTGA TTGACAACAT GCATCAATCG ACCTGCAGCC ACTCGAAGCG   3000

GCCGCGTTCA AGCTTCTGCA GGTCCGATGT GAGACTTTTC AACAAAGGGT AATATCCGGA   3060

AACCTCCTCG GATTCCATTG CCCAGCTATC TGTCACTTTA TTGTGAAGAT AGTGGAAAAG   3120

GAAGGTGGCT CCTACAAATG CCATCATTGC GATAAAGGAA AGGCCATCGT TGAAGATGCC   3180

TCTGCCGACA GTGGTCCCAA AGATGGACCC CCACCCACGA GGAGCATCGT GGAAAAAGAA   3240
```

```
GACGTTCCAA CCACGTCTTC AAAGCAAGTG GATTGATGTG ATGGTCCGAT GTGAGACTTT    3300

TCAACAAAGG GTAATATCCG GAAACCTCCT CGGATTCCAT TGCCCAGCTA TCTGTCACTT    3360

TATTGTGAAG ATAGTGGAAA AGGAAGGTGG CTCCTACAAA TGCCATCATT GCGATAAAGG    3420

AAAGGCCATC GTTGAAGATG CCTCTGCCGA CAGTGGTCCC AAAGATGGAC CCCCACCCAC    3480

GAGGAGCATC GTGGAAAAAG AAGACGTTCC AACCACGTCT TCAAAGCAAG TGGATTGATG    3540

TGATATCTCC ACTGACGTAA GGGATGACGC ACAATCCCAC TATCCTTCGC AAGACCCTTC    3600

CTCTATATAA GGAAGTTCAT TTCATTTGGA GAGGACACGC TGACAAGCTG ACTCTAGCAG    3660

ATCTCCATGG TCCGTCCTGT AGAAACCCCA ACCCGTGAAA TCAAAAAACT CGACGGCCTG    3720

TGGGCATTCA GTCTGGATCG CGAAAACTGT GGAATTGATC AGCGTTGGTG GGAAAGCGCG    3780

TTACAAGAAA GCCGGGCAAT TGCTGTGCCA GGCAGTTTTA ACGATCAGTT CGCCGATGCA    3840

GATATTCGTA ATTATGCGGG CAACGTCTGG TATCAGCGCG AAGTCTTTAT ACCGAAAGGT    3900

TGGGCAGGCC AGCGTATCGT GCTGCGTTTC GATGCGGTCA CTCATTACGG CAAAGTGTGG    3960

GTCAATAATC AGGAAGTGAT GGAGCATCAG GGCGGCTATA CGCCATTTGA AGCCGATGTC    4020

ACGCCGTATG TTATTGCCGG GAAAAGTGTA CGTATCACCG TTTGTGTGAA CAACGAACTG    4080

AACTGGCAGA CTATCCCGCC GGGAATGGTG ATTACCGACG AAAACGGCAA GAAAAAGCAG    4140

TCTTACTTCC ATGATTTCTT TAACTATGCC GGAATCCATC GCAGCGTAAT GCTCTACACC    4200

ACGCCGAACA CCTGGGTGGA CGATATCACC GTGGTGACGC ATGTCGCGCA AGACTGTAAC    4260

CACGCGTCTG TTGACTGGCA GGTGGTGGCC AATGGTGATG TCAGCGTTGA ACTGCGTGAT    4320

GCGGATCAAC AGGTGGTTGC AACTGGACAA GGCACTAGCG GGACTTTGCA AGTGGTGAAT    4380

CCGCACCTCT GGCAACCGGG TGAAGGTTAT CTCTATGAAC TGTGCGTCAC AGCCAAAAGC    4440

CAGACAGAGT GTGATATCTA CCCGCTTCGC GTCGGCATCC GGTCAGTGGC AGTGAAGGGC    4500

GAACAGTTCC TGATTAACCA CAAACCGTTC TACTTTACTG GCTTTGGTCG TCATGAAGAT    4560

GCGGACTTAC GTGGCAAAGG ATTCGATAAC GTGCTGATGG TGCACGACCA CGCATTAATG    4620

GACTGGATTG GGGCCAACTC CTACCGTACC TCGCATTACC CTTACGCTGA AGAGATGCTC    4680

GACTGGGCAG ATGAACATGG CATCGTGGTG ATTGATGAAA CTGCTGCTGT CGGCTTTAAC    4740

CTCTCTTTAG GCATTGGTTT CGAAGCGGGC AACAAGCCGA AGAACTGTA CAGCGAAGAG    4800

GCAGTCAACG GGGAAACTCA GCAAGCGCAC TTACAGGCGA TTAAAGAGCT GATAGCGCGT    4860

GACAAAAACC ACCCAAGCGT GGTGATGTGG AGTATTGCCA ACGAACCGGA TACCCGTCCT    4920

GCACGGGAAT ATTTCGGCAT TTCGCCACTG GCGGAAGCAA CGCGTAAACT CGACCCGACG    4980

CGTCCGATCA CCTGCGTCAA TGTAATGTTC TGCGACGCTC ACACCGATAC CATCAGCGAT    5040

CTCTTTGATG TGCTGTGCCT GAACCGTTAT TACGGATGGT ATGTCCAAAG CGGCGATTTG    5100

GAAACGGCAG AGAAGGTACT GGAAAAAGAA CTTCTGGCCT GGCAGGAGAA ACTGCATCAG    5160

CCGATTATCA TCACCGAATA CGGCGTGGAT ACGTTAGCCG GGCTGCACTC AATGTACACC    5220

GACATGTGGA GTGAAGAGTA TCAGTGTGCA TGGCTGGATA TGTATCACCG CGTCTTTGAT    5280

CGCGTCAGCG CCGTCGTCGG TGAACAGGTA TGGAATTTCG CCGATTTTGC GACCTCGCAA    5340

GGCATATTGC GCGTTGGCGG TAACAAGAAA GGGATCTTCA CTCGCGACCG CAAACCGAAG    5400

TCGGCGGCTT TTCTGCTGCA AAAACGCTGG ACTGGCATGA ACTTCGGTGA AAAACCGCAG    5460

CAGGGAGGCA AACAATGAAT CAACAACTCT CCTGGCGCAC CATCGTCGGC TACAGCCTCG    5520

GTGGGGAATT CGAGCTCGCC CGGGGATCCT CTAGCTAGAG CTTTCGTTCG TATCATCGGT    5580

TTCGACAACG TTCGTCAAGT TCAATGCATC AGTTTCATTG CGCACACACC AGAATCCTAC    5640
```

-continued

```
TGAGTTCGAG TATTATGGCA TTGGGAAAAC TGTTTTTCTT GTACCATTTG TTGTGCTTGT    5700
AATTTACTGT GTTTTTTATT CGGTTTTCGC TATCGAACTG TGAAATGGAA ATGGATGGAG    5760
AAGAGTTAAT GAATGATATG GTCCTTTTGT TCATTCTCAA ATTAATATTA TTTGTTTTTT    5820
CTCTTATTTG TTGTGTGTTG AATTTGAAAT TATAAGAGAT ATGCAAACAT TTTGTTTTGA    5880
GTAAAAATGT GTCAAATCGT GGCCTCTAAT GACCGAAGTT AATATGAGGA GTAAAACACT    5940
TGTAGTTGTA CCATTATGCT TATTCACTAG GCAACAAATA TATTTTCAGA CCTAGAAAAG    6000
CTGCAAATGT TACTGAATAC AAGTATGTCC TCTTGTGTTT TAGACATTTA TGAACTTTCC    6060
TTTATGTAAT TTTCCAGAAT CCTTGTCAGA TTCTAATCAT TGCTTTATAA TTATAGTTAT    6120
ACTCATGGAT TTGTAGTTGA GTATGAAAAT ATTTTTTAAT GCATTTTATG ACTTGCCAAT    6180
TGATTGACAA CATGCATCAA TCGACCTGCA GCCCAAGCTT GAGCTCAGGA TTTAGCAGCA    6240
TTCCAGATTG GGTTCAATCA ACAAGGTACG AGCCATATCA CTTTATTCAA ATTGGTATCG    6300
CCAAAACCAA GAAGGAACTC CCATCCTCAA AGGTTTGTAA GGAAGAATTC TCAGTCCAAA    6360
GCCTCAACAA GGTCAGGGTA CAGAGTCTCC AAACCATTAG CCAAAAGCTA CAGGAGATCA    6420
ATGAAGAATC TTCAATCAAA GTAAACTACT GTTCCAGCAC ATGCATCATG GTCAGTAAGT    6480
TTCAGAAAAA GACATCCACC GAAGACTTAA AGTTAGTGGG CATCTTTGAA AGTAATCTTG    6540
TCAACATCGA GCAGCTGGCT TGTGGGGACC AGACAAAAAA GGAATGGTGC AGAATTGTTA    6600
GGCGCACCTA CCAAAAGCAT CTTTGCCTTT ATTGCAAAGA TAAAGCAGAT TCCTCTAGTA    6660
CAAGTGGGGA ACAAAATAAC GTGGAAAAGA GCTGTCCTGA CAGCCCACTC ACTAATGCGT    6720
ATGACGAACG CAGTGACGAC CACAAAAGAA TTCCCTCTAT ATAAGAAGGC ATTCATTCCC    6780
ATTTGAAGGA TCATCAGATA CTGAACCAAT CCTTCTAGAA GATCTCCACA ATGGCTTCCT    6840
CTATGCTCTC TTCCGCTACT ATGGTTGCCT CTCCGGCTCA GGCCACTATG GTCGCTCCTT    6900
TCAACGGACT TAAGTCCTCC GCTGCCTTCC CAGCCACCCG CAAGGCTAAC AACGACATTA    6960
CTTCCATCAC AAGCAACGGC GGAAGAGTTA ACTGCATGCA GGTGTGGCCT CCGATTGGAA    7020
AGAAGAAGTT TGAGACTCTC TCTTACCTTC CTGACCTTAC CGATTCCGGT GGTCGCGTCA    7080
ACTGCATGCA GGCCATGGCT GAGAACCACA AGAAGGTTGG TATCGCTGGA GCTGGAATCG    7140
TTGGTGTTTG CACTGCTTTG ATGCTTCAAC GTCGTGGATT CAAGGTTACC TTGATTGATC    7200
CAAACCCACC AGGTGAAGGT GCTTCTTTCG GTAACGCTGG TTGCTTCAAC GGTTCCTCCG    7260
TTGTTCCAAT GTCCATGCCA GGAAACTTGA CTAGCGTTCC AAAGTGGCTT CTTGACCCAA    7320
TGGGTCCATT GTCCATCCGT TTCAGCTACT TTCCAACCAT CATGCCTTGG TTGATTCGTT    7380
TCTTGCTTGC TGGAAGACCA AACAAGGTGA AGGAGCAAGC TAAGGCACTC CGTAACCTCA    7440
TCAAGTCCAC TGTGCCTTTG ATCAAGTCCT TGGCTGAGGA GGCTGATGCT AGCCACCTTA    7500
TCCGTCACGA AGGTCACCTT ACCGTGTACC GTGGAGAAGC AGACTTCGCC AAGGACCGTG    7560
GAGGTTGGGA ACTTCGTCGT CTCAACGGTG TTCGTACTCA AATCCTCAGC GCTGATGCAT    7620
TGCGTGATTT CGATCCTAAC TTGTCTCACG CCTTTACCAA GGGAATCCTT ATCGAAGAGA    7680
ACGTCACAC CATCAACCCA CAAGGTCTCG TGACTCTCTT GTTTCGTCGT TTCATCGCTA    7740
ACGGTGGAGA GTTCGTGTCT GCTCGTGTTA TCGGATTCGA GACTGAAGGT CGTGCTCTCA    7800
AGGGTATCAC CACCACCAAC GGTGTTCTTG CTGTTGATGC AGCTGTTGTT GCAGCTGGTG    7860
CACACTCCAA GTCTCTTGCT AACTCCCTTG GTGATGACAT CCCATTGGAT ACCGAACGTG    7920
GATACCACAT CGTGATCGCC AACCCAGAAG CTGCTCCACG TATTCCAACT ACCGATGCTT    7980
```

| CTGGAAAGTT | CATCGCTACT | CCTATGGAGA | TGGGTCTTCG | TGTTGCTGGA | ACCGTTGAGT | 8040 |
| TCGCTGGTCT | CACTGCTGCT | CCTAACTGGA | AGCGTGCTCA | CGTTCTCTAC | ACTCACGCTC | 8100 |
| GTAAGTTGCT | TCCAGCTCTC | GCTCCTGCCA | GTTCTGAAGA | ACGTTACTCC | AAGTGGATGG | 8160 |
| GTTTCCGTCC | AAGCATCCCA | GATTCCCTTC | CAGTGATTGG | TCGTGCTACC | CGTACTCCAG | 8220 |
| ACGTTATCTA | CGCTTTCGGT | CACGGTCACC | TCGGTATGAC | TGGTGCTCCA | ATGACCGCAA | 8280 |
| CCCTCGTTTC | TGAGCTCCTC | GCAGGTGAGA | AGACCTCTAT | CGACATCTCT | CCATTCGCAC | 8340 |
| CAAACCGTTT | CGGTATTGGT | AAGTCCAAGC | AAACTGGTCC | TGCATCCTAA | GTGGGAATTC | 8400 |
| GAGCTCGGTA | CCGGATCC | | | | | 8418 |

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 6:

| CACCGGTCTT | TTGGAAGGTG | AAG | | | | 23 |

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 7:

| AACGAGACCC | ATAACGAGGA | AGC | | | | 23 |

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 8:

| AAACAGTCCC | GTGCATCCCC | AAC | | | | 23 |

(2) INFORMATION FOR SEQ ID NO: 9:

(i) SEQUENCE CHARACTERISTICS:
        (A) LENGTH: 23 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 9:

GACGCTCTCC TTGATTCTGT CCC                                              23

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 10:

CAAGAAGGTT GGTATCGCTG                                                  20

(2) INFORMATION FOR SEQ ID NO: 11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 11:

TCTTTTGTGG TCGTCACTGC GTT                                              23

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 12:

GCGAGCTCTA ATACGACTCA CTAT                                             24

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iii) ANTI-SENSE: NO (xi) SEQUENCE DESCRIPTION: SEQ ID NO: 13:

CGCGAGCTCA ATTAACCCTC ACT                                              23

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 14:

TCTGTACCCT GACCTTGTTG                                                  20

(2) INFORMATION FOR SEQ ID NO: 15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 15:

CGTGGATACC ACATCGTGAT                                                  20

(2) INFORMATION FOR SEQ ID NO: 16:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 16:

ACCTTGGCTT GAAGTACTC                                                   19

(2) INFORMATION FOR SEQ ID NO: 17:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 17:

TCAACCTACA GCTGATTTGG ACC                                          23

(2) INFORMATION FOR SEQ ID NO: 18:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 18:

GGACCGGAAC GACAATCTGA TC                                           22

(2) INFORMATION FOR SEQ ID NO: 19:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 19:

CTAGGGAAGT CCAAATCAGC CG                                           22

(2) INFORMATION FOR SEQ ID NO: 20:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 20:

TTTGGACCGG AACTTTCCAG AAG                                          23

(2) INFORMATION FOR SEQ ID NO: 21:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 21:

CTAACTTGCG CCATCGGAGA AAC                                              23

(2) INFORMATION FOR SEQ ID NO: 22:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 22:

GACTTGTCAC CTGGAATACG GAC                                              23

(2) INFORMATION FOR SEQ ID NO: 23:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 23:

ATTCTTGAGC TCATCAAGCA GCC                                              23

(2) INFORMATION FOR SEQ ID NO: 24:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 24:

AAGGTTGGTA TCGCTGGAGC TG                                               22

(2) INFORMATION FOR SEQ ID NO: 25:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 25:

TCTCCACAAT GGCTTCCTCT ATG                                              23

(2) INFORMATION FOR SEQ ID NO: 26:

(i) SEQUENCE CHARACTERISTICS:
        (A) LENGTH: 671 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 26:

```
CAAGATGGAT TGCACGCAGG TTCTCCGGCC GCTTGGGTGG AGAGGCTATT CGGCTATGAC      60
TGGGCACAAC AGACAATCGG CTGCTCTGAT GCCGCCGTGT TCCGGCTGTC AGCGCAGGGG     120
CGCCCGGTTC TTTTTGTCAA GACCGACCTG TCCGGTGCCC TGAATGAACT GCAGGACGAG     180
GCAGCGCGGC TATCGTGGCT GGCCACGACG GGCGTTCCTT GCGCAGCTGT GCTCGACGTT     240
GTCACTGAAG CGGGAAGGGA CTGGCTGCTA TTGGGCGAAG TGCCGGGGCA GGATCTCCTG     300
TCATCTCACC TTGCTCCTGC CGAGAAAGTA TCCATCATGG CTGATGCAAT GCGGCGGCTG     360
CATACGCTTG ATCCGGCTAC CTGCCCATTC GACCACCAAG CGAAACATCG CATCGAGCGA     420
GCACGTACTC GGATGGAAGC CGGTCTTGTC GATCAGGATG ATCTGGACGA AGAGCATCAG     480
GGGCTCGCGC CAGCCGAACT GTTCGCCAGG CTCAAGGCGC GCATGCCCGA CGGCGAGGAT     540
CTCGTCGTGA CCCATGGCGA TGCCTGCTTG CCGAATATCA TGGTGGAAAA TGGCCGCTTT     600
TCTGGATTCA TCGACTGTGG CCGGCTGGGT GTGGCGGACC GCTATCAGGA CATAGCGTTG     660
GCTACCCGTG A                                                         671
```

(2) INFORMATION FOR SEQ ID NO: 27:

(i) SEQUENCE CHARACTERISTICS:
        (A) LENGTH: 739 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 27:

```
GGACCGGAAC GACAATCTGA TCCCCATCAA GCTTGAGCTC AGGATTTAGC AGCATTCCAG      60
ATTGGGTTCA ATCAACAAGG TACGAGCCAT ATCACTTTAT TCAAATTGGT ATCGCCAAAA     120
CCAAGAAGGA ACTCCCATCC TCAAAGGTTT GTAAGGAAGA ATTCTCAGTC CAAAGCCTCA     180
ACAAGGTCAG GGTACAGAGT CTCCAAACCA TTAGCCAAAA GCTACAGGAG ATCAATGAAG     240
AATCTTCAAT CAAAGTAAAC TACTGTTCCA GCACATGCAT CATGGTCAGT AAGTTTCAGA     300
AAAAGACATC CACCGAAGAC TTAAAGTTAG TGGGCATCTT TGAAAGTAAT CTTGTCAACA     360
TCGAGCAGCT GGCTTGTGGG GACCAGACAA AAAAGGAATG GTGCAGAATT GTTAGGCGCA     420
CCTACCAAAA GCATCTTTGC CTTTATTGCA AGATAAAGC AGATTCCTCT AGTACAAGTG     480
GGGAACAAAA TAACGTGGAA AAGAGCTGTC CTGACAGCCC ACTCACTAAT GCGTATGACG     540
AACGCAGTGA CGACCACAAA AGAATTCCCT CTATATAAGA AGGCATTCAT TCCCATTTGA     600
```

-continued

```
AGGATCATCA GATACTGAAC CAATCCTTCT AGAAGATCTA AGCTTATCGA TAAGCTTGAT      660

GTAATTGGAG GAAGATCAAA ATTTTCAATC CCCATTCTTC GATTGCTTCA ATTGAAGTTT      720

CTCCGATGGC GCAAGTTAG                                                   739
```